US012637705B2

(12) United States Patent
Guan et al.

(10) Patent No.: US 12,637,705 B2
(45) Date of Patent: May 26, 2026

(54) SAMPLE PREPARATION AND VIRAL DETECTION METHODS

(71) Applicant: The United States of America, as represented by the Secretary, Department of Health and Human Services, Bethesda, MD (US)

(72) Inventors: Bin Guan, Rockville, MD (US); Robert B. Hufnagel, Washington, DC (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 645 days.

(21) Appl. No.: 18/041,295

(22) PCT Filed: Aug. 12, 2021

(86) PCT No.: PCT/US2021/045675
§ 371 (c)(1),
(2) Date: Feb. 10, 2023

(87) PCT Pub. No.: WO2022/036046
PCT Pub. Date: Feb. 17, 2022

(65) Prior Publication Data
US 2023/0323425 A1      Oct. 12, 2023

Related U.S. Application Data

(60) Provisional application No. 63/065,931, filed on Aug. 14, 2020.

(51) Int. Cl.
*C12Q 1/6806* (2018.01)
(52) U.S. Cl.
CPC ................................. *C12Q 1/6806* (2013.01)
(58) Field of Classification Search
CPC .................................................. C12Q 1/6806
See application file for complete search history.

(56) References Cited

FOREIGN PATENT DOCUMENTS

| EP | 3 636 769 A1 | 4/2020 |
| WO | WO 02/44400 A2 | 6/2002 |

OTHER PUBLICATIONS

Vijay, S., and C. S. Chauhan, 2014, Ion exchange resins and their applications, J. Drug. Deliv. Therapeutics, 4(4):115-123.*
Anand, V., et al., Sep. 2001, Ion-exchange resins: carrying drug delivery forward, DDT 6(17):905-914.*
"CDC 2019—Novel Coronavirus (2019-nCoV) Real Time RT-PCR Diagnostic Panel," Instructions For Use, Catalog # 2019-nCoVEUA- 01, 1000 reactions, Document No. CDC-006-00019, Revision: 05, Effective: Jul. 13, 2020 (59 pages).
Batèjat et al., Heat inactivation of the Severe Acute Respiratory Syndrome Coronavirus 2, bioRxiv preprint doi: https://doi.org/10. 1101/2020.05.01.067769. this version posted May 1, 2020 (5 pages).
Beltrán-Pavez et al., "SARS-CoV-2 detection from nasopharyngeal swab samples without RNA extraction," bioRxiv preprint doi: https://doi.org/10.1101/2020.03.28.013508. this version posted Mar. 30, 2020 (5 pages).
Bruce et al., "Direct RT-qPCR detection of SARS-CoV-2 RNA from patient nasopharyngeal swabs without an RNA extraction step," bioRxiv preprint doi: https://doi.org/10.1101/2020.03.20.001008. this version posted Apr. 6, 2020 (14 pages).
Coombs et al., "Optimisation of DNA and RNA extraction from archival formalin-fixed tissue," *Nucl Acids Res.* 27:e12, 1999 (3 pages).
De Lamballerie et al., "A one-step microbial DNA extraction method using "Chelex 100" suitable for gene amplification," *Res Micobiol.* 143:785-790, 1992.
Fomsgaard et al., "An alternative workflow for molecular detection of SARS-CoV-2—escape from the NA extraction kit-shortage, Copenhagen, Denmark, Mar. 2020," medRxiv preprint doi: https://doi.org/10.1101/2020.03.27.20044495.this version posted Mar. 30, 2020 (8 pages).
Guan et al., "Sensitive extraction-free SARS-CoV-2 RNA virus detection using a chelating resin", *iScience* 24(9):102960, Sep. 24, 2021, (17 pages).
Guan et al., "Sensitive extraction-free SARS-CoV-2 RNA virus detection using a novel RNA preparation method," DOI: 10.1101/ 2021.01.29.21250790 external link Feb. 1, 2021 (Feb. 1, 2021), Retrieved from the Internet: URL:https://www.medrxiv.org/content/ 10.1101/2021.01.29.21250790v1.full.pdf; XP055859457; DOI: 10.1101/ 2021.01.29.21250790 external link [retrieved on Nov. 9, 2021] (34 pages).
Hale et al., "Comparison of four RNA extraction methods for the detection of small round structured viruses in faecal specimens," *J Virol. Methods* 57:195-201, 1996.
Howson et al., "Defining the relative performance of isothermal assays that can be used for rapid and sensitive detection of foot-and-mouth disease virus," *J Virol. Methods* 249:102-110, 2017.
International Search Report and Written Opinion mailed on Jan. 24, 2022 for International Application No. PCT/US2021/045675 (21 pages).
Johnson et al., "Abundant variation in microsatellites of the parasitic nematode Trichostrongylus tenuis and linkage to a tandem repeat," *Mol Biochem Parasitol.* 148:210-218, 2006.
Nishiguchi et al., "DNA Isolation Procedures," in Techniques in Molecular Systematics and Evolution, ed. By Rob DeSalle et al., Verlag Birkhäuser Basel/Switzerland, pp. 245-287, 2002.
Rekland et al., "Detection of viral sequences in archival spinal cords from fatal cases of poliomyelitis in 1951-1952," *J Virol.* 114:91-96, 2003.

(Continued)

*Primary Examiner* — Jeffrey S Parkin
(74) *Attorney, Agent, or Firm* — Klarquist Sparkman, LLP

(57) ABSTRACT

Methods of sample preparation for detection of nucleic acids (such as viral nucleic acids, for example, viral RNA) are provided. In some examples, the methods include contacting a sample with a solution including a buffer containing about 0-0.5 mM EDTA and a chelating resin and incubating the resulting mixture at a temperature of at least about 55° C.

26 Claims, 24 Drawing Sheets
Specification includes a Sequence Listing.

(56) References Cited

OTHER PUBLICATIONS

Shiaw et al., "Evaluation of DNA and RNA Extraction Methods," *Med J. Malaysia* 65:133-137, 2010.

Srivatsan et al., "Preliminary support for a "dry swab, extraction free" protocol for SARS-CoV-2 testing via RT-qPCR," bioRxiv preprint doi: https://doi.org/10.1101/2020.04.22.056283. this version posted Apr. 23, 2020 (11 pages).

Srivatsan et al., "SwabExpress: An end-to-end protocol for extraction-free COVID-19 testing," DOI: 10.1101/2020.04.22.056283 external link, Apr. 23, 2020 (Apr. 23, 2020), Retrieved from the Internet: URL:https://www.ncbi.nlm.nih.gov/pmc/articles/PMC7263496.1/pdf/nihpp-2020.04.22.056283.pdf XP055860661; DOI: 10.1101/2020.04.22.056283 external link, [retrieved on Nov. 12, 2021] (43 pages).

Sweet et al., "An Improved Method to Recover Saliva from Human Skin: The Double Swab Technique", Jan. 1, 1997 (Jan. 1, 1997), p. 320-322.

* cited by examiner

FIG. 9B $CH_2COOH$     $CH_2COOH$        $CH_2COO^-$        $CH_2COO^-$ $\varnothing\text{-}CH_2\text{-}NH^+$   $\varnothing\text{-}CH_2\text{-}NH^+$   $\varnothing\text{-}CH_2\text{-}NH^+$    $\varnothing\text{-}CH_2\text{-}N$ $CH_2COOH$     $CH_2COO^-$        $CH_2COO^-$        $CH_2COO^-$ pH 2.21 ⟶ pH 3.99 ⟶ pH 7.41 ⟶ pH 12.30

$\varnothing:$    $-CH-CH2-$

FIG. 10B

SEQUENCE LISTING

<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: 2019nCoV_N1F primer

<400> SEQUENCE: 1
gaccccaaaa tcagcgaaat                                       20

<210> SEQ ID NO 2
<211> LENGTH: 24
<212> TYPE: DNA
<213> ORGANISM: Artificial Sequence
<220> FEATURE:
<223> OTHER INFORMATION: 2019nCoV_N1R primer

<400> SEQUENCE: 2
tctggttact gccagttgaa tctg                                  24

<210> SEQ ID NO 3
<211> LENGTH: 24
<212> TYPE: DNA
<213> ORGANISM: Artificial Sequence
<220> FEATURE:
<223> OTHER INFORMATION: 2019-nCoV_N1Fam probe

<400> SEQUENCE: 3
accccgcatt acgtttggtg gacc                                  24

<210> SEQ ID NO 4
<211> LENGTH: 20
<212> TYPE: DNA
<213> ORGANISM: Artificial Sequence
<220> FEATURE:
<223> OTHER INFORMATION: 2019-nCoV_N2-F primer

<400> SEQUENCE: 4
ttacaaacat tggccgcaaa                                       20

<210> SEQ ID NO 5
<211> LENGTH: 18
<212> TYPE: DNA
<213> ORGANISM: Artificial Sequence
<220> FEATURE:
<223> OTHER INFORMATION: 2019-nCoV_N2-R primer

<400> SEQUENCE: 5
gcgcgacatt ccgaagaa                                         18

<210> SEQ ID NO 6
<211> LENGTH: 23
<212> TYPE: DNA
<213> ORGANISM: Artificial Sequence
<220> FEATURE:
<223> OTHER INFORMATION: 2019-nCoV_N2Fam probe

<400> SEQUENCE: 6
acaatttgcc cccagcgctt cag                                   23

<210> SEQ ID NO 7
<211> LENGTH: 19
<212> TYPE: DNA
<213> ORGANISM: Artificial Sequence
<220> FEATURE:
<223> OTHER INFORMATION: RPP30F primer

<400> SEQUENCE: 7
agatttggac ctgcgagcg                                        19

<210> SEQ ID NO 8

-continued

```
<211> LENGTH: 20
<212> TYPE: DNA
<213> ORGANISM: Artificial Sequence
<220> FEATURE:
<223> OTHER INFORMATION: RPP30R primer

<400> SEQUENCE: 8
gagcggctgt ctccacaagt                                          20

<210> SEQ ID NO 9
<211> LENGTH: 23
<212> TYPE: DNA
<213> ORGANISM: Artificial Sequence
<220> FEATURE:
<223> OTHER INFORMATION: RPP30Hex probe

<400> SEQUENCE: 9
ttctgacctg aaggctctgc gcg                                      23

<210> SEQ ID NO 10
<211> LENGTH: 22
<212> TYPE: DNA
<213> ORGANISM: Artificial Sequence
<220> FEATURE:
<223> OTHER INFORMATION: RPP30cR primer

<400> SEQUENCE: 10
gcaacaactg aatagccaag gt                                       22

<210> SEQ ID NO 11
<211> LENGTH: 20
<212> TYPE: DNA
<213> ORGANISM: Artificial Sequence
<220> FEATURE:
<223> OTHER INFORMATION: chr5UC-F primer

<400> SEQUENCE: 11
atttatgacc agccacagcc                                          20

<210> SEQ ID NO 12
<211> LENGTH: 20
<212> TYPE: DNA
<213> ORGANISM: Artificial Sequence
<220> FEATURE:
<223> OTHER INFORMATION: chr5UC-R primer

<400> SEQUENCE: 12
ccatcaggga cttggtttca                                          20

<210> SEQ ID NO 13
<211> LENGTH: 23
<212> TYPE: DNA
<213> ORGANISM: Artificial Sequence
<220> FEATURE:
<223> OTHER INFORMATION: chr5UC-Hex probe

<400> SEQUENCE: 13
caactccagc agctgcacac cgc                                      23
```

SAMPLE PREPARATION AND VIRAL DETECTION METHODS

CROSS REFERENCE TO RELATED APPLICATIONS

This application is the U.S. National Stage of International Application No. PCT/US2021/045675, filed Aug. 12, 2021, which was published in English under PCT Article 21(2), which in turn claims the benefit of U.S. Provisional Application No. 63/065,931, filed Aug. 14, 2020, which are incorporated herein by reference in their entireties.

ACKNOWLEDGMENT OF GOVERNMENT SUPPORT

This invention was made with government support under project number Z01#: AEY000564-01 awarded by the National Institutes of Health, National Eye Institute. The government has certain rights in the invention.

INCORPORATION OF SEQUENCE LISTING

The Sequence Listing is submitted as a TXT file in the form of the file named 4239-104930-03_ST25.TXT, which was created on Feb. 1, 2023, and is 2840 bytes, which is incorporated by reference herein in its entirety.

FIELD

This disclosure relates to sample preparation methods for viral nucleic acid detection, particularly viral RNA detection.

BACKGROUND

Conventional detection of SARS-CoV-2 involves collection of a patient sample with a nasopharyngeal swab, storage of the swab in a transport medium, extraction of RNA, and nucleic acid detection, such as by quantitative reverse transcription PCR (RT-qPCR). However, these procedures are time consuming, costly, and are hampered by shortages of reagents and supplies.

SUMMARY

There is a need for simplified viral nucleic acid testing procedures that retain assay sensitivity and specificity. Disclosed herein are sample preparation methods that in some examples do not require an RNA extraction step (e.g., RNA extraction-free methods). The disclosed methods preserve viral RNA in the sample and permit direct detection (e.g., by RT-qPCR or RT-ddPCR methods).

In some embodiments, the disclosed methods include contacting a sample with a solution that includes a buffer at pH 4-10, 0-0.5 mM EDTA, and 1-50% chelating resin to form a mixture and incubating the mixture at a temperature of at least 55° C. for about 1-60 minutes. In some examples, the solution includes about 10 mM Tris-HCl and about 0.1 mM EDTA. In some embodiments, the solution further includes dimethylsulfoxide (DMSO), such as about 10-99% DMSO.

In other embodiments, the methods include contacting a sample with a solution that includes about 10-100% DMSO and 1-50% chelating resin to form a mixture, and incubating the mixture at a temperature of at least 55° C. for about 1-60 minutes. In some examples, the solution includes about 40% DMSO or about 50% DMSO.

In additional embodiments, the methods include contacting a sample with a solution including about 0.1-0.5 M urea and 1-50% chelating resin to form a mixture, and incubating the mixture at a temperature of at least 55° C. for about 1-60 minutes. In one example, the solution includes about 0.5 M urea.

In further embodiments, the methods include contacting the sample with a solution that includes Hanks Balanced Salt Solution (HBSS), 2% fetal bovine serum, and 1-50% chelating resin to form a mixture, and incubating the mixture at a temperature of at least 55° C. for about 1-60 minutes. In some examples, the HBSS includes calcium and/or magnesium, while in other examples, the HBSS does not include added calcium and/or magnesium.

The chelating resin utilized in the methods provided herein in some examples is capable of chelating divalent cations and may include any one of Chelex® 100, Chelex® 20, iminodiacetate resin SIR-300, aminophosphonic resin SIR-500, bis-picolylamine resin, iminodiacetic acid Sepharose® resin, or iminodiacetic acid agarose resin. In some examples, the chelating resin is covalently linked to a magnetic core (such as a magnetic bead). In specific examples, the chelating resin is an iminodiacetate resin, for example, Chelex® 100, such as about 5% Chelex® 100.

In some embodiments, the methods include incubating the mixture at about 95-100° C. for about 3-5 minutes. In other embodiments, the methods include incubating the mixture at about 65° C. for about 15 minutes.

The sample utilized in the disclosed methods is a biological specimen or an environmental sample. In some examples, the sample is a nasopharyngeal swab, an oropharyngeal swab, a mid-turbinate swab, saliva, urine, stool, or buccal cells.

In some embodiments, the mixture is stored for a period of time following incubating the mixture at a temperature of at least 55° C. for about 1-60 minutes. In some examples, the mixture is stored at ambient temperature or at about 4° C. (for example for about 2 hours to 7 days or more). In other embodiments, the mixture is stored for a period of time prior to incubating at a temperature of at least about 55° C. In some examples, the mixture is stored at ambient temperature or at about 4° C. (for example for about 2 hours to 7 days or more).

In additional embodiments, the methods further include detecting one or more nucleic acids (such as RNA, for example, viral RNA) in the mixture. Detecting one or more nucleic acids in the mixture includes utilizing real-time quantitative PCR, digital droplet PCR, reverse transcription real-time quantitative PCR, or reverse transcription-digital droplet PCR, in some examples.

Also provided are kits including one or more containers including a disclosed solution for use in the methods of sample preparation provided herein. In some examples, the kit includes one or more containers (such as one or more tubes or vials) including a solution comprising 10 mM Tris-HCl, 0.1 mM EDTA, and 5% Chelex® 100, and optionally 10-99% DMSO; 10-50% dimethylsulfoxide (DMSO) and 5% Chelex® 100; 0.1-0.5 M urea and 5% Chelex® 100; or Hanks Balanced Salt Solution (HBSS), 2% fetal bovine serum, and 5% Chelex® 100. The kits may also include additional reagents for the disclosed methods, such as one or more buffers, enzymes, nucleic acid primers, and nucleic acid probes.

The foregoing and other features of the disclosure will become more apparent from the following detailed description, which proceeds with reference to the accompanying figures.

BRIEF DESCRIPTION OF THE DRAWINGS

FIG. 1A: 200,000 SARS-Cov-2 virions and 20,000 293FT cells were dried at room temperature in a speedvac and then resuspended in 200 µl lowTE buffer to mimic the dry swab. The same amount of virions and 293FT cells directly added to 200 µl lowTE buffer was used to mimic the wet swab. The samples expected to have 1000 virion genome copies/µl were then used directly for RT-ddPCR (No Heat), heated at 98° C. for 5 min (Heat), or heated with 5% Chelex® 100 (Heat_Chelex®100). The RT-ddPCR reactions were carried out in one well for N1 and cRPP30 and another well for N2 and RPP30. FIG. 1B: Negative controls and virion samples prepared as wet swab. The mean genome copies/µl of N1 and N2 were less than 1.2 in negative controls without virions added. Copies/µl refers to concentration in the samples used for RT-ddPCR. The error bars represent Poisson 95% confidence intervals. Dashed line indicates the threshold for the low detection limit of 1.8 copies/µl of SARS-CoV-2 virions. FIG. 1C: Virions of 1000 genome copies/µl and 100 293FT cells/µl were prepared in lowTE, $H_2O$, MEM alpha, or TED10, treated and assayed by RT-ddPCR as in FIG. 1A. FIG. 1D: Virions of 1000 genome copies/µl and 100 293FT cells/µl were prepared in lowTE, HBSS (with or without 1.3 mM $Ca^{2+}$ and 0.9 mM $Mg^{2+}$) with 2% FBS, PBS, or M4 viral transport medium, treated and assayed by RT-ddPCR in a four-plex assay for N1, N2, cRPP30 and a genomic DNA region on chromosome 5.

FIG. 5A: RNA refers to RNA prepared by simulating conventional method with RNA-extraction: a swab was added to 3 ml of VTM, of which 200 µl were used for RNA extraction, and RNA was eluted in 50 µl $H_2O$. 5 µl RNA was then used for RT-qPCR in 20 µl reaction volume. Other samples were heated in 5% Chelex® 100 before RT-qPCR. 5 µl of samples were used for one reaction RT-qPCR except that 2.5 µl of MEM alpha samples were used. Ct (Crossing threshold) values for N1 & N2 (viral targets) were set at 0.1 ΔRn, Ct values for cRPP30 (specific for RPP30 cDNA) and RPP30 (targets both genomic DNA and cDNA) were at 0.02 ΔRn. Samples were diluted in $H_2O$. Samples with undetermined Ct values were plotted as Ct 40. FIG. 5B: Optimization of the NEB Luna RT-qPCR assay. Extracted RNA samples were serial diluted and assayed either using 2.5 µl sample in a 10 reaction volume or 5 µl in a 20 µl reaction, and using a longer PCR protocol (I: 10 seconds of denature and 40 seconds of annealing/extension) or a shorter PCR protocol (II: 5 seconds of denature and 20 seconds of annealing/extension). NTC, no-template control. FIG. 5C: RT-qPCR comparing Chelex-RNA and conventional RNA extraction. RNA refers to RNA prepared by simulating conventional method with RNA-extraction: a swab with 200,000 to 200 genome copies of SARS-CoV-2 virions was added to 3 ml of VTM, of which 200 µl were used for RNA extraction, and RNA was eluted in 50 µl H2O. LowTE refers to simulating a swab with 200,000 to 200 genome copies of virions eluted in 200 µl lowTE, and then heated in the presence of 5% Chelex. FIG. 5D: RT-qPCR comparing Chelex and Proteinase K methods for saliva samples. 1000 to 1 genome copies/µl of SARS-CoV-2 virions were prepared in saliva samples and subjected to the Chelex or Proteinase K methods and RT-qPCR. The NEB Luna RT-qPCR kit and NEB-Luna-Program II was used with 2.5 µl samples in 10 µl reaction volume. Samples with undetermined Ct values were plotted as Ct 40.

FIG. 7A: Virions of 1000 virion genome copies/µl and 100 cells/µl 293FT cells were prepared in lowTE, TED10, or MEM alpha, and stored at room temperature. Samples were heated with 5% Chelex® 100 on the time points indicated and assayed. The RT-ddPCR reactions were carried out in one well for N1 and cRPP30 and another well for N2 and RPP30. FIG. 7B: Virions of 1000 virion genome copies/µl and 100 cells/µl 293FT cells were prepared in various buffers, heated with 5% Chelex® 100 on day 0, and assayed on a time series. Copies/µl refers to concentration in the samples used for RT-ddPCR. The error bars represent Poisson 95% confidence intervals.

FIG. 8A: Virions were added to saliva samples at 1000 virion genome copies/μl and stored at room temperature. Samples were heated with 1/5 volumes of 50% Chelex® 100 prepared in $H_2O$ or TED99 on the time points indicated and assayed. The RT-ddPCR reactions were carried out in one well for N1 and cRPP30 and another well for N2 and RPP30. FIGS. 8B and 8C: Virions of 1000 virion genome copies/μl were prepared in saliva as in FIG. 8A, heated with Chelex® 100 on day 0 or day 3, and assayed on the days indicated. cRPP30 data points were not plotted because of the low level detected. Copies/μl refers to concentration in the samples used for RT-ddPCR. The error bars represent Poisson 95% confidence intervals.

FIGS. 9A-9B show 2.5-5% DMSO decreased negative droplet intensity in RT-ddPCR assays. The RT-ddPCR reactions containing 0%, 2.5%, or 5% DMSO were performed for a sample using N1 and cRPP30 (FIG. 9A) or N2 and RPP30 (FIG. 9B). The Channel 1 on y-axis denotes N1 or N2. The channel 2 on x-axis denotes cRPP30 or RPP30.

FIGS. 10A-10B illustrate the chemical structures of Chelex® and proposed magnetic chelating resins. FIG. 10A: Chelex® structure at different pH. Below pH 4, the resin does not have selectivity to divalent ions. The styrene divinylbenzene group is represented by ø. Modified from Chelex® 100 and Chelex 20 Chelating Ion Exchange Resin Instruction Manual, www.bio-rad.com/webroot/web/pdf/lsr/literature/LIT200.pdf. FIG. 10B: Proposed chemical structure of magnetic Chelating beads. Top, Paired iminodiacetate ions act as chelating groups in binding polyvalent metal ions. Middle, Aminophosphonic chelant. Bottom, Picolyamine chelant.

FIG. 11A: Patient NP swab samples were heated in the presence of 5% Chelex (501 to S16, and S19, S20) or 10% Chelex (S17 & S18). S19 & S20 are 1:2 dilution of S17 & S18 in LowTE, respectively. FIG. 11B: 50 μl of patient saliva samples (Saliva01 & 02) or negative patient saliva samples spiked with positive patient saliva samples (Salia03 to 22) were mixed with 25 μl of 50% Chelex in TED99, and heated for 5 min in a ThermoMixer. FIG. 11C: Paired NP swabs from seven patients (P1 to P7) and saliva-saturated swabs from four patients (P4 to P7) were collected in VTM or Chelex collection tubes. VTM samples were used for RNA extraction (EasyMag). Luna refers to the NEB Luna RT-qPCR kit and NEB-Luna-Program II with 2.5 μl samples in a 10 μl reaction volume. CL refers to CDC assay performed in the clinical laboratory with 5 μl samples in a 20 μl reaction volume. Undetermined Ct values were plotted as Ct 40.

SEQUENCE LISTING

Figure 1A:
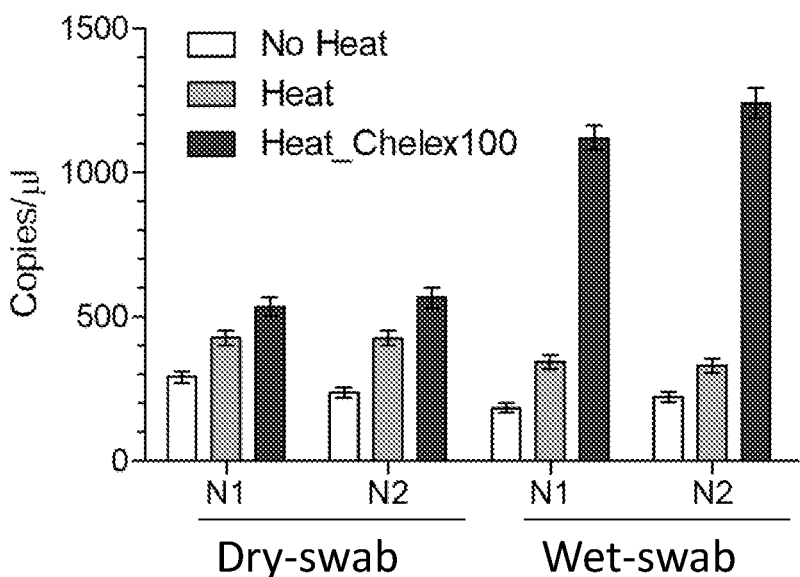
FIGS. 1A-1D show RT-ddPCR assays comparing the dry- and wet-swab and different RNA extraction-free methods for SARS-CoV-2 detection.
Figure 1A:
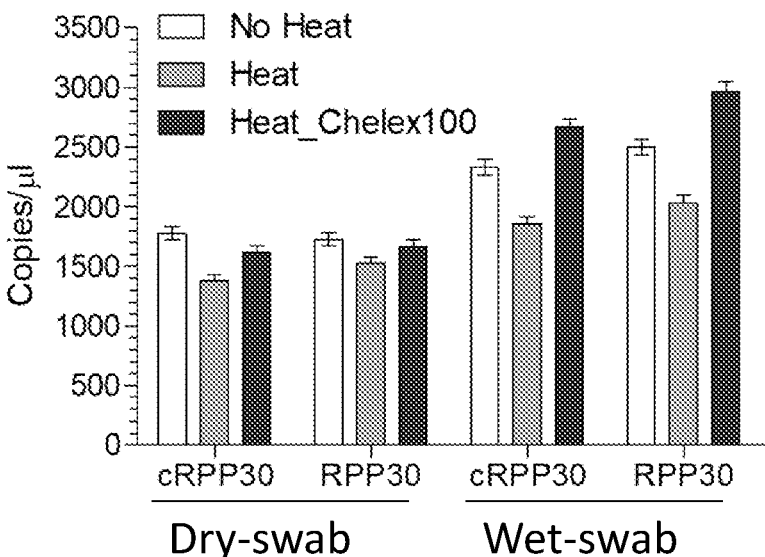

Any nucleic acid and amino acid sequences listed herein or in the accompanying Sequence Listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

SEQ ID NOs: 1 and 2 are the nucleic acid sequence of 2019nCoV N1 forward and reverse primers, respectively.

SEQ ID NO: 3 is the nucleic acid sequence of a 2019nCoV N1 probe.

SEQ ID NOs: 4 and 5 are the nucleic acid sequence of 2019nCoV N2 forward and reverse primers, respectively.

SEQ ID NO: 6 is the nucleic acid sequence of a 2019nCoV N2 probe.

SEQ ID NOs: 7 and 8 are the nucleic acid sequence of human RPP30 forward and reverse primers, respectively.

SEQ ID NO: 9 is the nucleic acid sequence of a human RPP30 probe.

SEQ ID NO: 10 is the nucleic acid sequence of a primer spanning exon 1 and exon 2 of RPP30.

SEQ ID NOs: 11 and 12 are the nucleic acid sequence of forward and reverse primers for an ultra-conserved region in human chromosome 5, respectively.

SEQ ID NO: 13 is the nucleic acid sequence of a probe for an ultra-conserved region in human chromosome 5.

DETAILED DESCRIPTION

Previous efforts to use crude clinical samples directly for RT-qPCR detection of SARS-CoV-2 and ZIKA viruses have shown promising results (Srivatsan et al., doi.org/10.1101/2020.04.22.056283, 2020; Li et al., *Int. J. Infect. Dis.* 85:167-174, 2019).

However, the potential inhibitors to reverse-transcription and/or PCR present in clinical samples may lead to lower sensitivity. Optimizing assay conditions by testing different types of Taq enzymes and PCR reaction buffers has shown promise but is a complicated and time-consuming process (Li et al., *Int. J. Infect. Dis.* 85:167-174, 2019). In addition, unprocessed samples may lead to more RNA degradation during sample collection and storage.

Disclosed herein are sample preparation methods using a chelating resin (such as Chelex® 100 resin) that demonstrates increased RNA yield available for RT-qPCR and RT-ddPCR detection compared to conventional methods in nearly all sample conditions. The disclosed methods are amenable for high-throughput processing, expected to shorten diagnostic testing time, and reduce testing costs for RNA viruses (including, but not limited to SARS-CoV-2). The sample preparation methods provided could also be used together with other RNA detection methods such as rolling circle amplification, loop-mediated isothermal amplification, or SHERLOCK (Kellner et al., *Nat. Protoc.* 14:2986-3012, 2019).

The disclosed methods demonstrate improved yield compared to previous methods, including up to 100% yield in some conditions, and high sensitivity. Additional advantages of the disclosed methods include low reagent costs, room temperature stability, and improved safety (due to inclusion of a heat inactivation step). In addition, omission of an RNA extraction step conserves laboratory reagents and supplies, which have been in limited supply during the COVID-19 pandemic. This method also provides decreased cost per sample for RNA extraction methods and reduces the overall end-to-end diagnostic testing time by 30-60 minutes. Additionally, there is decreased environmental and/or chemical waste from the RNA extraction step, including kit packaging and disposables, such as pipette tips.

I. Terms

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes X*, published by Jones & Bartlett Publishers, 2009; and Meyers et al. (eds.), *The Encyclopedia of Cell Biology and Molecu-*

*lar Medicine*, published by Wiley-VCH in 16 volumes, 2008; and other similar references.

The singular terms "a," "an," and "the" include plural referents unless the context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Chelating resin: A resin that includes ligands that can bind metal cations. Exemplary chelating resins include iminodiacetate (e.g., SIR-300), aminophosphonic (e.g., SIR-500), and picolyamine (e.g., DOW 4196). In some examples, chelating resins also include an ion exchange functionality, for example as a copolymer with the metal ion binding ligand. Chelex® is an exemplary chelating resin that includes an ion exchange functionality.

Chelex® resin: Chelex® is a chelating ion exchange resin of styrene divinylbenzene copolymer containing paired iminodiacetate ions, which act as chelating groups in binding polyvalent metal ions. Chelex® is a chelating agent that is highly selective for divalent metal ions compared to monovalent metal ions. Chelex® (such as Chelex®100 and Chelex® 20) is commercially available from Bio-Rad (Hercules, CA).

Contacting: Placement in direct physical association; includes both in solid and liquid form.

Sample: A specimen containing nucleic acids (for example, DNA, RNA, and/or mRNA), proteins, or combinations thereof. Examples include, but are not limited to, biological samples, such as peripheral blood, serum, plasma, urine, saliva, sputum, stool, nasopharyngeal swab, cells, tissue biopsy, fine needle aspirate, surgical specimen, and autopsy material. In some examples, a sample includes nasopharyngeal swab, saliva, or urine. A sample may also include environmental samples, for example, food, water, surface swabs, or other materials that may contain or be contaminated with a virus.

Subject: A living multi-cellular vertebrate organism, a category that includes human and non-human mammals, including livestock and companion animals.

II. Methods of Sample Preparation and Viral Detection

Disclosed herein are methods of sample preparation, for example for detection of nucleic acids (such as viral nucleic acids, for example, viral RNA). Also provided are methods of detecting nucleic acids (such as viral nucleic acids, for example, viral RNA) including steps of sample preparation and detection. In particular embodiments, the methods do not include extraction of RNA (for example, to obtain a relatively pure preparation of RNA molecules) from the sample prior to detection.

In some embodiments, the methods include contacting a sample with a solution including a buffer containing about 0-0.5 mM EDTA and a chelating resin and incubating the resulting mixture at a temperature of at least about 55° C. In additional embodiments, at least a portion of the mixture is then used for nucleic acid detection, such as RNA detection.

In some embodiments, the solution includes a buffer that can maintain pH of the solution between about 1-10, for example, about pH 4-10. In some examples, the buffer is Tris, HEPES, MOPS, phosphate buffer (e.g., phosphate buffered saline), or Hanks balanced salt solution. In one non-limiting example, the buffer is Tris-HCl (such as about 1-100 mM Tris-HCl, for example, about 1-10 mM Tris-HCl, about 5-20 mM Tris-HCl, about 15-30 mM Tris-HCl, about 25-50 mM Tris-HCl, about 40-70 mM Tris-HCl, about 60-80 mM Tris-HCl, about 75-90 mM Tris-HCl, or about 85-100 mM Tris-HCl). In one non-limiting example, the buffer is 10 mM Tris-HCl.

In some embodiments, the solution includes 0 to 0.5 mM EDTA, such as 0-0.1 mM, about 0.05-0.2 mM, about 0.1-0.25 mM, about 0.2-0.4 mM, or about 0.3-0.5 mM EDTA. In particular non-limiting examples, the solution includes about 0.1 mM EDTA.

The solution also includes a chelating resin capable of chelating divalent cations. In some examples, the chelating resin is Chelex® (Bio-Rad), iminodiacetate resin SIR-300 (ResinTech, West Berlin, NJ), aminophosphonic resin SIR-500 (ResinTech), bis-picolylamine resin (e.g., AMBERSEP™ M4195 resin (Dupont)), iminodiacetic acid Sepharose® (Sigma-Aldrich), or iminodiacetic acid agarose (Sigma-Aldrich). In some examples, the solution includes Chelex® 100 (e.g., 200-400 mesh, 50-100 mesh, or 100-200 mesh) or Chelex® 20. In one non-limiting example, the solution includes Chelex® 100. In some examples, the solution includes about 1-50% of the chelating resin, such as about 1-10%, about 5-20%, about 10-30%, about 25-40%, or about 35-50% (for example, about 1%, about 2.5%, about 5%, about 7.5%, about 10%, about 15%, about 20%, about 25%, about 30%, about 35%, about 40%, about 45%, or about 50%). In one non-limiting example, the solution includes about 5% Chelex® 100.

Figure 10A:
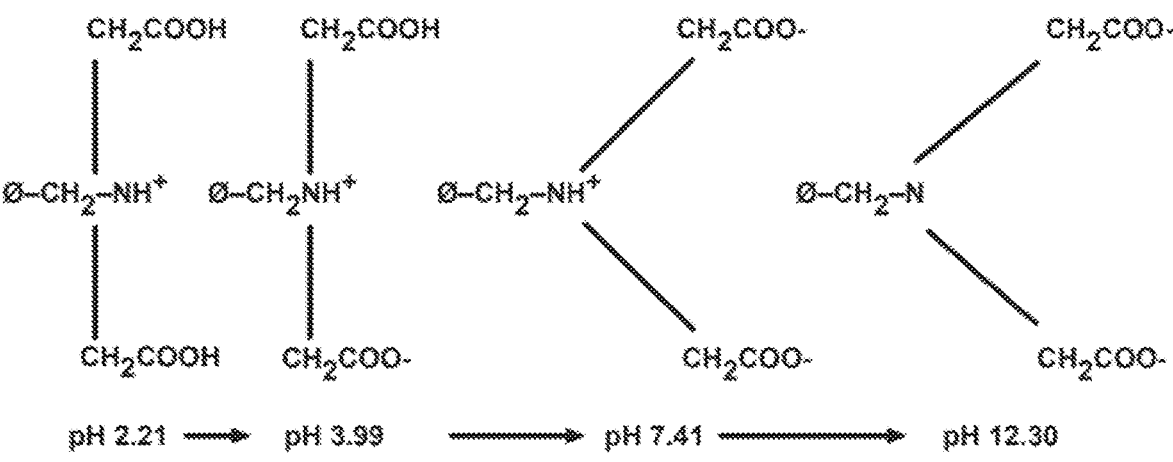
Figure 10B:
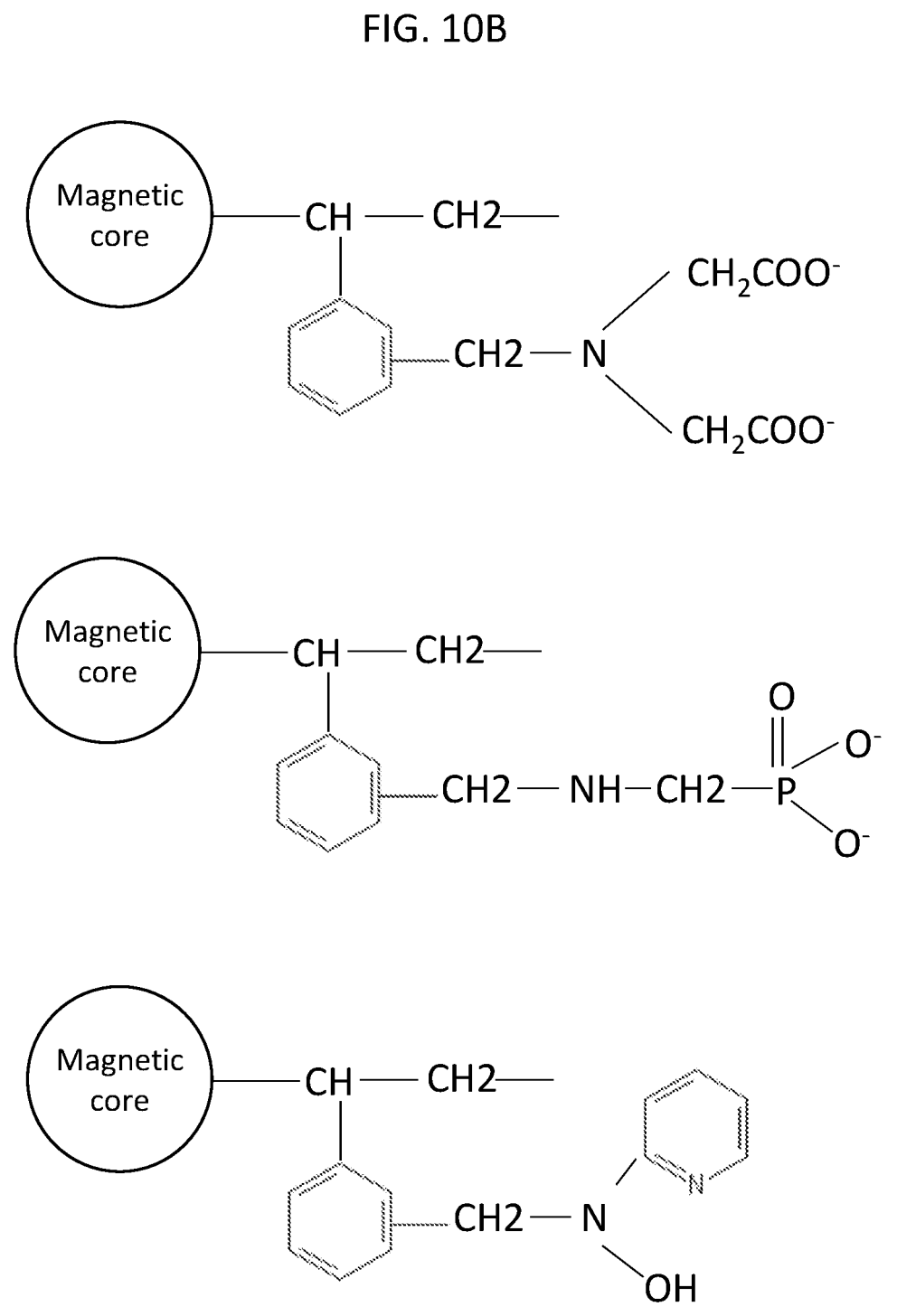

In other embodiments, the chelating resin in the solution is covalently linked to a magnetic core (such as a magnetic bead). Exemplary embodiments are illustrated in FIG. 10B. The magnetic core can be made of magnetite which is covalently linked to the styrene divinylbenzene copolymer. The magnetic core (e.g., beads) can be either ferri- (or ferro-) magnetic or superparamagnetic. In embodiments of the disclosed methods including chelating resin covalently linked to magnetic beads, a magnet is used to separate the magnetic chelating beads from solution containing RNA (for example, instead of a centrifugation step).

In some embodiments, the solution includes a buffer (including, but not limited to Tris-HCl) with a pH of about 1-10, such as about 2-9, about 4-10, about 4-8, or about 5-8.5 (such as about 5.0-6.5, about 5.5-7.0, about 6.0-7.5, about 7.0-8.0, or about 8.0-8.5, for example, about 5.0, about 5.5, about 6.0, about 6.5, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, or about 8.5).

In some specific embodiments, the methods include contacting a sample with a solution including about 10 mM Tris-HCl and about 0.1 mM EDTA ("low TE" buffer) and 1-50% Chelex® 100. In one non-limiting example, the sample is contacted with 10 mM Tris-HCl, pH 8.0, 0.1 mM EDTA, and 5% Chelex® 100. In another non-limiting example, the sample is contacted with 10 mM Tris-HCl, pH 7.5, 0.1 mM EDTA, and 5% Chelex® 100.

In additional embodiments, the solution including a buffer, 0-0.5 mM EDTA and 1-50% chelating resin further includes dimethylsulfoxide (DMSO). In some examples, the solution includes about 10-99% DMSO (such as about 10-40%, about 20-50%, about 30-60%, about 40-70%, about 50-80%, about 60-90%, or about 70-99%). In particular, non-limiting examples, the solution includes about 10% DMSO, about 40% DMSO, about 50% DMSO, or about 99% DMSO. In one non-limiting example, the sample is contacted with 10 mM Tris-HCl, pH 8.0, 0.1 mM EDTA, 99% DMSO, and 50% Chelex®.

In other embodiments, the methods include contacting a sample with DMSO, urea, MEM alpha, or viral transport medium (VTM) and 1-50% chelating resin (such as 1-50% Chelex®) and incubating the resulting mixture at a temperature of at least about 55° C. In some examples, at least a portion of the mixture is then used for nucleic acid detection, such as RNA detection.

In some examples, the sample is contacted with about 2.5-100% DMSO (for example, about 2.5-5%, about 5-10%, about 10-25%, about 15-40%, about 30-60%, about 40-70%, about 50-80%, about 70-95%, or about 90-100%, for example, about 2.5%, about 5%, about 10%, about 12.5%, about 25%, about 40%, about 50% DMSO, about 60%, about 70%, about 80%, about 90%, about 95%, about 95%, or about 100%) and about 1-50% chelating resin (such as Chelex®) and then incubated at a temperature of at least about 55° C. In one non-limiting example, the sample is contacted with about 50% DMSO and about 5% Chelex® 100 and then is incubated at a temperature of at least 55° C. In another non-limiting example, the sample is contacted with about 40% DMSO and about 5% Chelex® 100 and then is incubated at a temperature of at least 55° C.

In other examples, the sample is contacted with about 0.1-0.5 M urea (for example, about 0.1-0.25 M, about 0.2-0.4 M, or about 0.3-0.5 M, for example, about 0.1 M, about 0.125 M, about 0.25 M, about 0.4 M, or about 0.5 M urea) and about 1-50% chelating resin (such as Chelex®) and then incubated at a temperature of at least about 55° C. In one non-limiting example, the sample is contacted with about 0.5 M urea and about 5% Chelex® 100 and then is incubated at a temperature of at least 55° C.

In another example, the sample is contacted with MEM alpha and about 1-50% chelating resin (such as Chelex®) and then incubated at a temperature of at least about 55° C. MEM alpha is commercially available. In some examples, the MEM alpha is supplemented with FBS and antibiotics (such as about 2% fetal bovine serum, 100 μg/ml Gentamicin and 0.5% Amphotericin B). In one non-limiting example, the sample is contacted with MEM alpha and about 5% Chelex® 100 and then is incubated at a temperature of at least 55° C. In another non-limiting example, the sample is contacted with MEM alpha dilated 1:2 and about 5% Chelex® 100 and then is incubated at a temperature of at least 55° C.

In further examples, the sample is contacted with VTM and about 1-50% chelating resin (such as Chelex®) and then incubated at a temperature of at least about 55° C. In some examples, VTM includes Hanks Balanced Salt Solution (HBSS) and 2% fetal bovine serum, and optionally 100 μg/ml Gentamicin and 0.5% Amphotericin B (see, e.g., cdc.gov/coronavirus/2019-ncov/downloads/Viral-Transport-Medium.pdf). In one non-limiting example, the sample is contacted with VTM and about 5% Chelex® 100 and then is incubated at a temperature of at least 55° C.

Exemplary combinations of Chelex® 100 and buffers and/or other reagents that can be used in the disclosed methods are provided in Table 1. These combinations and the indicated concentrations are only examples, and should not be considered to be limiting.

TABLE 1

Exemplary Chelex ® 100/buffer combinations

| Name | Chelex ® 100 (final conc.) | Buffer/Other reagents (final conc.) |
|---|---|---|
| Low TE | 5% | 10 mM Tris-HCl pH 8.0 0.1 mM EDTA |
| TED10 | 5% | Low TE + 10% DMSO |
| TED40 | 5% | Low TE + 40% DMSO |
| TED99 | 5% | Low TE + 99% DMSO |
| DMSO | 5% | 10-100% DMSO |
| Urea | 5% | 0.1-0.5M |
| MEM alpha | 5% | Minimal essential medium alpha |
| VTM | 5% | Hanks Balanced Salt Solution (HBSS), 2% fetal bovine serum, 100 μg/ml Gentamicin, 0.5% Amphotericin B |
| PBS | 5% | Phosphate buffered saline (1x) |
| M4 | 5% | MicroTest ™ M4 ™ contains gelatin, vancomycin, amphotericin B, and colistin |

The mixture of the sample and solution is incubated at a temperature of at least about 55° C. (for example, about 55-100° C., such as about 55-70° C., about 60-80° C., about 65-85° C., about 75-90° C., or about 90-100° C.) for a period of time. In some non-limiting examples, the mixture is heated at a temperature and for a period of time sufficient to inactive virus (such as coronavirus) in the sample. In some examples, the sample is heated at about 55-65° C. (for example, about 55° C., about 56° C., about 57° C., about 58° C., about 59° C., about 60° C., about 61° C., about 62° C., about 63° C., about 64° C., or about 65° C.). In other examples, the mixture is incubated at about 95-100° C. (for example, about 95° C., about 96° C., about 97° C., about 98° C., about 99° C., or about 100° C.). In some non-limiting examples, the mixture is incubated at about 98° C. In some examples, the mixture is incubated at a temperature of at least about 55° C. for about 1-60 minutes (such as about 1-5 minutes, 5-10 minutes, about 8-12 minutes, about 10-15 minutes, about 12-20 minutes, about 18-25 minutes, about 25-30 minutes, about 25-40 minutes, about 35-45 minutes, about 40-50 minutes, about 45-55 minutes, or about 50-60 minutes) for example about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, or 60 minutes). In one non-limiting example, the mixture is incubated at 98° C. for 5 minutes. In another non-limiting example, the mixture is incubated at 95° C. for 5 minutes. In other non-limiting examples, the mixture is incubated at 65° C. for about 15 minutes. One of ordinary skill in the art can select an appropriate combination of temperature and time (see, e.g., Batejat et al., doi.org/10.1101/2020.05.01.067769, 2020). In other embodiments, a shorter period of time (for example, 1 minute or less) may be utilized, for example, if using a micro-fluidic device with close contact of heating source and sample.

In some embodiments, contacting the sample with the solution (such as one of those listed in Table 1) includes placing the sample in the solution following collection. In some examples, a swab (such as a nasopharyngeal swab or oropharyngeal swab) is placed in a container with the solution or rinsed in the solution and removed. In other examples, a liquid sample (such as saliva) is placed in a container with the solution. In some examples, the sample is diluted in the solution about 1:1, about 1:2, about 1:4, or about 1:8. In one non-limiting example, the sample (e.g., saliva) is diluted 1:1 with the solution. In such examples, the sample is placed is a solution such that the final concentration of the components is as described herein. For example, if a sample is diluted 1:1 with the solution, the starting solution is a 2× concentration.

In some embodiments, the sample is contacted with the solution (such as one of those listed in Table 1) for a period of time before incubating at a temperature of at least about 55° C. In some examples, the sample is contacted with the solution and is stored at ambient temperature (including, but not limited to room temperature, for example, about 20-25° C.) or at about 4° C. for a period of time (such as for storage or transport) before incubating at a temperature of at least about 55° C. In some examples, the sample is contacted with the solution for about 2 hours to 7 days before incubating at a temperature of at least about 55° C., such as about 2 hours to 12 hours, about 8 hours to 16 hours, about 12 hours to 24 hours, about 1 to 3 days, about 2 to 4 days, about 3 to 5 days, about 4 to 6 days, or about 5 to 7 days (for example, about 2 hours, about 4 hours, about 8 hours, about 12 hours, 16 hours, about 1 day, about 2 days, about 3 days, about 4 days, about 5 days, about 6 days or about 7 days). In other examples, the sample is contacted with the solution for about 7 days or more (such as about 7, 8, 9, 10, 11, 12, 13, 14 days or more) before incubating at a temperature of at least about 55° C. In particular examples, the sample is contacted with low TE, TED10, or TED99 and Chelex® 100 and stored for about 1-5 days prior to incubating at a temperature of at least about 55° C.

In other embodiments, the sample is contacted with the solution (such as one of those listed in Table 1) and incubated at a temperature of at least about 55° C., then stored at ambient temperature or at about 4° C. for a period of time before nucleic acid detection. In some examples, the sample is contacted with the solution and incubated at a temperature of at least about 55° C., then stored for about 2 hours to 7 days, such as about 2 hours to 12 hours, about 8 hours to 16 hours, about 12 hours to 24 hours, about 1 to 3 days, about 2 to 4 days, about 3 to 5 days, about 4 to 6 days, or about 5 to 7 days (for example, about 2 hours, about 4 hours, about 8 hours, about 12 hours, about 16 hours, about 1 day, about 2 days, about 3 days, about 4 days, about 5 days, about 6 days or about 7 days). In other examples, the sample is contacted with the solution and incubated at a temperature of at least about 55° C., then stored for about 7 days or more (such as about 7, 8, 9, 10, 11, 12, 13, 14 days or more).

In some examples, contacting the sample with the solution is adding the sample to a solution that includes the chelating resin (such as Chelex®). In other examples, contacting the sample with the solution is adding the sample to a solution without the chelating resin, then mixing with the chelating resin (such as Chelex®). For example, the chelating resin may be added to the mixture immediately prior to incubating the mixture at a temperature of at least 55° C.

In some embodiments, the sample is from a subject (such as a subject suspected to be infected with a virus) or an environmental sample. Appropriate samples include any environmental or biological samples, including clinical samples obtained from a human or veterinary subject. Suitable samples include but are not limited to, bodily fluids (for example, blood, serum, urine, cerebrospinal fluid, middle ear fluids, bronchoalveolar lavage, tracheal aspirates, sputum, nasopharyngeal aspirates, oropharyngeal aspirates, or saliva), mid-turbinate swabs, nasopharyngeal swabs, oropharyngeal swabs, eye swabs, cervical swabs, vaginal swabs, rectal swabs, stool and stool suspensions, hair, cells (e.g., buccal cells), tissues, and autopsy samples. Suitable samples also include environmental samples including, but not limited to, food, water, surface swabs, or other materials that may contain or be contaminated with a virus.

In some embodiments, the methods are utilized to detect nucleic acids from an RNA virus in the sample. RNA viruses include positive-strand RNA viruses, negative-strand RNA viruses, and retroviruses. Exemplary positive-strand RNA viruses include, but are not limited to: Picornaviruses, such as Aphthoviridae (for example foot-and-mouth-disease virus (FMDV)), Cardioviridae; Enteroviridae (such as Coxsackie viruses, Echoviruses, Enteroviruses, and Polioviruses); Rhinoviridae (Rhinoviruses); Hepataviridae (Hepatitis A viruses); Togaviruses (examples of which include rubella; alphaviruses (such as Chikungunya virus, Western equine encephalitis virus, Eastern equine encephalitis virus, and Venezuelan equine encephalitis virus); Flaviviruses (such as Dengue viruses, West Nile virus, Japanese encephalitis virus, Zika virus, and tick-borne encephalitis viruses); Noroviruses (such as Norwalk virus); and Coronaviruses (examples of which include SARS-CoV-2 (2019-nCoV), SARS-CoV, and MERS-CoV, as well as alpha coronaviruses, beta coronaviruses, and gamma coronaviruses). Exemplary negative-strand RNA viruses include, but are not limited to: Orthomyxoviruses (such as the influenza virus), Rhabdoviruses (such as Rabies virus), and Paramyxoviruses (examples of which include measles virus, respiratory syncytial virus, and parainfluenza viruses). Exemplary retroviruses include human immunodeficiency viruses (for example, HIV-1 and HIV-2). One of ordinary skill in the art can identify additional RNA viruses that can be detected utilizing the methods provided herein.

In some embodiments, following sample treatment, at least a portion of the heated mixture is used for nucleic acid detection (such as RNA detection). In some examples, the mixture is used directly in the detection method without further processing (e.g., is "RNA extraction-free"). In other examples, the mixture is subject to additional processing steps, such as RNA extraction (for example, using phenol/chloroform extraction or a commercially available RNA purification kit). In some embodiments, the mixture is centrifuged or allowed to stand for a time prior to using a portion of the mixture for nucleic acid detection (for example, to separate the chelating resin from the solution). In other embodiments, the chelating resin is linked to a magnetic bead, and a magnet is used to separate the chelating resin from the solution.

In some examples, the nucleic acid is RNA. RNA is in some examples detected by a nucleic acid amplification method, such as reverse transcription PCR (RT-PCR), quantitative RT-PCR (qRT-PCR), reverse transcription digital droplet PCR (RT-ddPCR); reverse transcription-loop-mediated isothermal amplification (RT-LAMP); strand displacement amplification (see U.S. Pat. No. 5,744,311); rolling circle amplification; SHERLOCK (Kellner et al., *Nat. Protoc.* 14:2986-3012; 2019); transcription-mediated amplification; transcription-free isothermal amplification; repair chain reaction amplification; ligase chain reaction amplification; gap filling ligase chain reaction amplification; coupled ligase detection and PCR; and NASBA™ RNA transcription-free amplification. In particular non-limiting examples, RNA detection is by qRT-PCR or RT-ddPCR.

The sample preparation solutions and methods provided herein provide for highly sensitive detection of viral nucleic acids in a sample, and in some examples do not require nucleic acid extraction (such as RNA extraction) prior to detection. In some examples, samples prepared using the disclosed methods permit detection of viral nucleic acid in a sample with a limit of detection (LOD) of about 200,000 genome copies or less, for example, about 20,000 genome copies or less, about 2000 genome copies or less, or 200 genome copies or less. In other examples, samples prepared using the disclosed methods permit detection of viral nucleic acid in a sample with a limit of detection (LOD) of about 1000 virus copies/µl or less, about 100 virus copies/µl or less, about 10 virus copies/µl or less, about 2 virus copies/µl or less, or even 1 virus copy/µl.

III. Kits

Kits including one or more solutions for performing the methods disclosed herein are also provided. In some embodiments, the kits include at least one container including a solution for use in the disclosed methods (including, but not limited to the solutions provided in Table 1). In some embodiments, the Chelex® (or other chelating resin) is covalently linked to magnetic beads.

In some examples, the kits include one or more containers (such as one or more tubes or vials) including a solution including 10 mM Tris-HCl, 0.1 mM EDTA, and 5% chelating resin (such as Chelex® 100). In additional examples, the kits include one or more containers (such as one or more tubes or vials) including a solution including 10 mM Tris-HCl, 0.1 mM EDTA, 50% chelating resin (such as Chelex® 100). In other examples, the kits include one or more containers (such as one or more tubes or vials) including a solution including 10 mM Tris-HCl, 0.1 mM EDTA, 10% DMSO, and 5% chelating resin (such as Chelex® 100). In further examples, the kits include one or more containers (such as one or more tubes or vials) including a solution including 10 mM Tris-HCl, 0.1 mM EDTA, 40% DMSO, and 5% chelating resin (such as Chelex® 100). In additional examples, the kits include one or more containers (such as one or more tubes or vials) including a solution including 10 mM Tris-HCl, 0.1 mM EDTA, 99% DMSO, and 50% chelating resin (such as Chelex® 100).

In other examples, the kits include one or more containers (such as one or more tubes or vials) including a solution including 50% DMSO and 5% chelating resin (such as Chelex® 100). In further examples, the kits include one or more containers (such as one or more tubes or vials) including a solution including 0.5 M urea and 5% chelating resin (such as Chelex® 100). In still further examples, the kits include one or more containers (such as one or more tubes or vials) including a solution including VTM and 5% chelating resin (such as Chelex® 100).

In some embodiments, the kits include one or more containers (such as one or more tubes or vials) including the solution at a 2× concentration, such that addition of a liquid sample at a 1:1 dilution provides the final concentration of the solution (such as those included in Table 1). In other examples, the solution is included at a 5× concentration or a 10× concentration.

In some embodiments, the kits further include one or more buffers, enzymes, or other reagents for use in the disclosed methods, for example, including one or more reagents for nucleic acid detection (such as viral RNA detection). In some examples, the kits include one or more of nucleic acid primers or probes (for example, for amplification and/or detection of viral RNA), reverse transcriptase (RT) and/or RT buffer, DNA polymerase and/or DNA polymerase buffer, and RNase-free water. These additional reagents may be included in individual containers or in a mixture. For example, buffer(s) and enzyme(s) may be included in a single container as a mixture. In some embodiments, the kits further include instructions for use.

EXAMPLES

The following examples are provided to illustrate certain particular features and/or embodiments. These examples should not be construed to limit the disclosure to the particular features or embodiments described.

Example 1

Materials and Methods

Chemicals and buffers: Chelex® 100 Resin (cat #142-1253, molecular biology grade) was obtained from Bio-Rad. Molecular biology grade water (cat #351-029-101), TE pH 8.0 (cat #351-011-131), 1 M Tris-HCl pH 7.5 (cat #351-006-101) were from Quality Biological (Gaithersburg, MD). The low-EDTA TE ("low TE") buffer (10 mM Tris, pH 8.0, 0.1 mM EDTA, cat #12090-015), Urea (cat #15505-050), RNAlater (cat #AM7024), MEM Alpha medium (cat #12571-063), HBSS (cat #14175-095, no Ca$^{2+}$/Mg$^{2+}$), M4 (M4, cat #R12550) were from Thermo Fisher Scientific. Dimethyl sulfoxide (DMSO, cat #D2650-100ML) was from Sigma. 1 M Tris-HCl pH 8.0 (cat #221-232) and 0.5 M EDTA (cat #221-057) were from Crystalgen (Commack, NY). PBS (cat #RGF-3190, pH 7.2) was from KD Medical (Columbia, MD). TED10 buffer was 90% low TE and 10% DMSO (volume to volume). TED99 was 10 mM Tris pH8.0, 0.1 mM EDTA and 99% DMSO, which was made by mixing 100 µl of 1 M Tris pH 8.0, 2 µl of 0.5 M EDTA, and 9.9 ml of DMSO.

Primers, RT-qPCR and RT-ddPCR: The primer and probe sequences used for detecting SARS-CoV-2 targets were N1 and N2 designed by the CDC (cdc.gov/coronavirus/2019-ncov/lab/rt-per-panel-primer-probes.html). Their sequences are 2019nCoV_N1F: GACCCCAAAATCAGCGAAAT (SEQ ID NO: 1), 2019nCoV_N1R: TCTGGT-TACTGCCAGTTGAATCTG (SEQ ID NO: 2), 2019-nCoV_N1Fam: ACCCCGCATTACGTTTGGTGGACC (SEQ ID NO: 3); 2019-nCoV_N2-F: TTACAAACAT-TGGCCGCAAA (SEQ ID NO: 4), 2019-nCoV_N2-R: GCGCGACATTCCGAAGAA (SEQ ID NO: 5), 2019-nCoV_N2Fam: ACAATTTGCCCCCAGCGCTTCAG (SEQ ID NO: 6). The RPP30 (Rnase P) primer and probe sequences used to amplify human cellular RNA are also from the CDC protocol, whose sequences are RPP30F: AGATTTGGACCTGCGAGCG (SEQ ID NO: 7), RPP30R: GAGCGGCTGTCTCCACAAGT (SEQ ID NO: 8), RPP30Hex: TTCTGACCTGAAGGCTCTGCGCG (SEQ ID NO: 9). This pair of RPP30 primers amplifies the DNA sequence located in the exon 1 of the RPP30 gene, and thus is expected to amplify both cDNA and genomic DNA contents. An additional RPP30 primer specific for RPP30 cDNA was also designed to span the exon 1 and exon 2, RPP30cR: GCAACAACTGAATAGCCAagGT (SEQ ID NO: 10), where lower case denotes the exon junction. RPP30cR was used for RT-qPCR or -ddPCR together with RPP30F and RPP30Hex. The primer and probe sequences for an ultra-conserved region in chromosome 5 are: chr5UC-F ATTTATGACCAGCCACAGCC (SEQ ID NO:

11), chr5UC-R CCATCAGGGACTTGGTTTCA (SEQ ID NO: 12), chr5UC-Hex CAACTCCAGCAGCTGCACACCGC (SEQ ID NO: 13. Primers and probes were ordered from Eurofins Genomics.

The Luna Universal Probe One-Step RT-qPCR Kit (#E3006X, NEB) was used for RT-qPCR with the following cycling conditions using a QuantStudio 3 real-time PCR system (ThermoFisher Scientific): 55° C. for 10 min, 95° C. for 1 min, and 45 cycles of 95° C. for 10 sec and 60° C. for 40 sec. Ct (Crossing threshold) values for N1 & N2 (viral targets) were set at 0.1 ΔRn, Ct values for cRPP30 (specific for RPP30 cDNA) and RPP30 (targets both genomic DNA and cDNA) were set at 0.02 ΔRn. The 1-Step RT-ddPCR Advanced Kit for Probes (#186-4021, Bio-Rad) was used for RT-ddPCR using the QX200 Droplet Digital PCR System (Bio-Rad). If DMSO was not present in the sample, DMSO was added to 2.5% in the reaction. The cycling condition for RT-ddPCR was: 50° C. for 60 min, 95° C. for 10 min, and 40 cycles of 94° C. for 10 sec and 55° C. for 60 sec, followed by 98° C. for 10 min, 4° C. for 30 min then hold at 4° C.

Preparation of SARS-CoV-2 virus: The heat-inactivated SARS-CoV-2 virions were obtained from ATCC (VR-1986HK, lot 70035039, $3.75 \times 10^5$ genome copies/μl measured by ddPCR at ATCC) and used for making various dilutions of materials for testing. The conventional RNA-extraction RT-qPCR method was exemplified by the following procedures: a swab was added to 3 ml of VTM (viral transport medium, also known as universal transport medium or UTM, such as CDC-recommended HBSS with 2% FBS and 100 μg/ml Gentamicin and 0.5% Amphotericin B), of which 200 μl were used for RNA extraction, and RNA was eluted in 50 μl $H_2O$. Then, 5 μl RNA was used for RT-qPCR in 20 μl reaction volume. The Qiagen RNeasy® mini kit was used on less than 10 μl virion and cell mixture that contained the expected amounts of virions as in the "conventional" method.

Chelex® 100 was first prepared in $H_2O$ at 50% (50 grams/100 ml total volume, or 500 milligrams Chelex® 100 to 550 μl $H_2O$). The 50% Chelex® was then added in 1/10 volume to samples to obtain 5% Chelex® in a PCR strip or PCR plate with a wide-bore tip. The samples were vortexed briefly then heated in a PCR cycler for 5 min at 98° C., followed by spinning at 2,000×g for 2 mins in a swing-rotor. The supernatant was then used for RT-qPCR or -ddPCR. Chelex® 100 was also prepared in low TE or TED99 at 50%.

Example 2

Detection of Virion RNA in Different Buffer Compositions with Chelex®

Figure 1B:
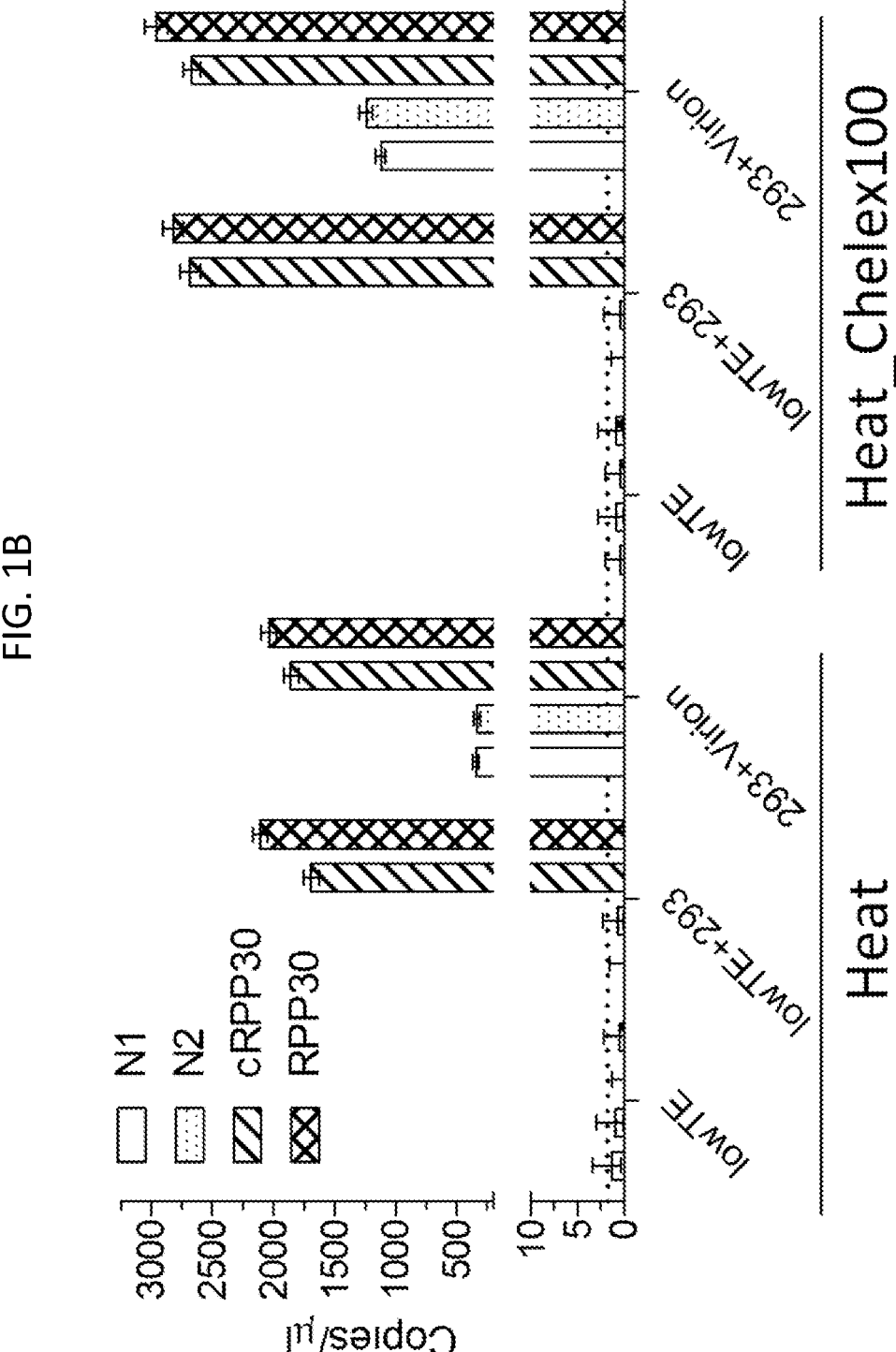

Given previous results for COVID-19 testing obtained by direct elution of dried patient swab to low TE (lx low-EDTA TE, 10 mM Tris, 0.1 mM EDTA, pH 8.0) buffer (Srivatsan et al., doi.org/10.1101/2020.04.22.056283, 2020), we set out to repeat the direct elution of dried swab procedure. The COVID-19 dry swab test procedure was simulated by drying down a mixture of inactivated SARS-CoV-2 virions with known genome copies and 293FT cells in a speedvac centrifuge at room temperature, and then resuspending the virus and cells in lowTE at 1,000 genome copies/μl. We then quantified the virus with RT-ddPCR using the N1 and N2 primers, which showed that only ~30% of virions were detected (FIG. 1A, dried swab, no heat). Because heating has been shown to increase testing sensitivity for SARS-CoV-2 samples stored in viral transport media (Beltran- Pavez et al., doi.org/10.1101/2020.03.28.013508, 2020; Bruce et al., doi.org/10.1101/2020.03.20.001008, 2020; Fomsgaard et al., this .doi.org/10.1101/2020.03.27.20044495), we also tested the heating condition and found that heating increased the detected virion to ~40% of added virions (FIG. 1A, dried swab, heat). As RNases are $Mg^{2+}$-dependent similar to DNases, and Chelex® 100 resin has been used successfully for DNA preparation for its property of chelating divalent ions (Walsh et al., BioTechniques 10:506-513, 1991), we heated the sample along with 5% Chelex® 100. Chelex® 100 improved detected virions to ~50% (FIG. 1A, dried swab, Heat_Chelex®100). We suspected that the drying/resuspension process caused viral and cellular RNA degradation, thus, we added the virions and 293FT cells directly to lowTE and measured viral RNA content (FIG. 1A, wet swab). Heating the sample in lowTE in the presence of Chelex® 100 led to the detection of ~100% of the virions added. The RPP30 mRNA also had the highest yield in the presence of Chelex® 100. The heating condition without Chelex® 100 led to more RPP30 mRNA degradation as compared to no heat condition. In contrast, heating with Chelex® 100 led to better detection of the SARS-CoV-2 RNA as well as RPP30 mRNA. The N1, N2 primers produced minimum background as shown in the lowTE or lowTE plus 293FT cells controls (FIG. 1B).

Figure 1C:
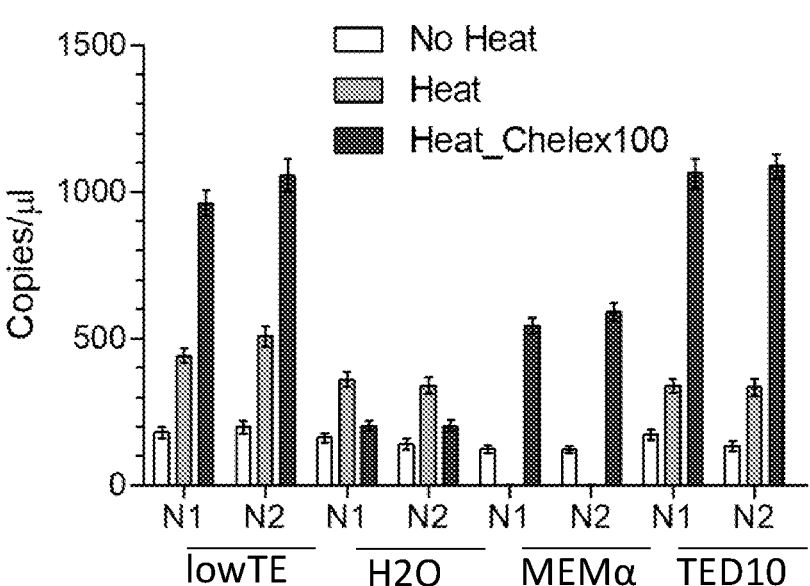
Figure 1C:
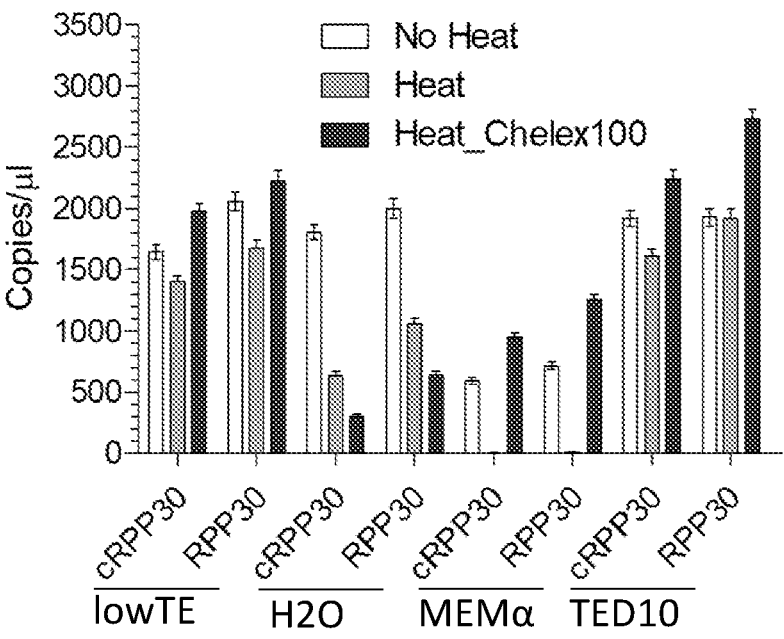
Figure 9A:
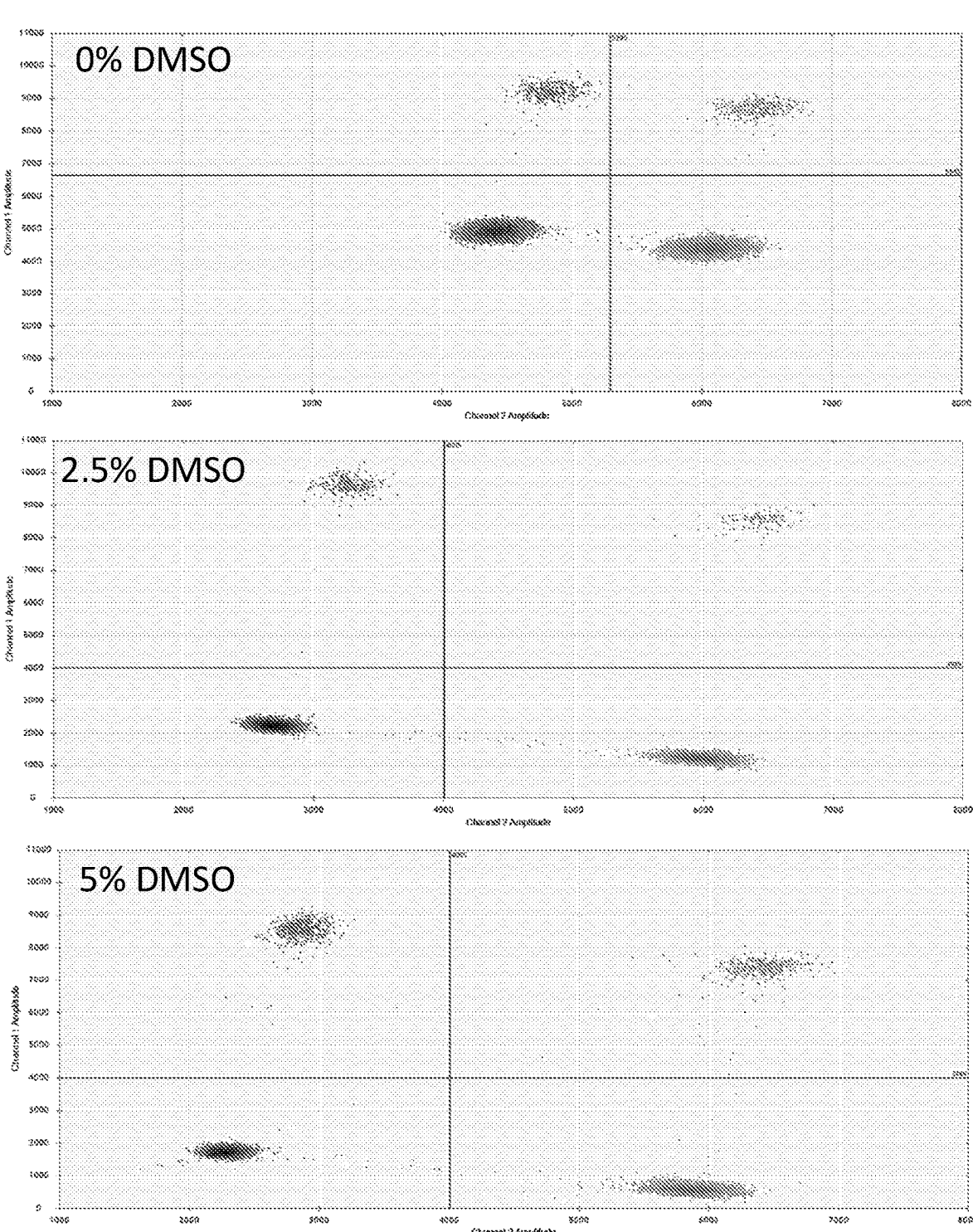
Figure 9B:
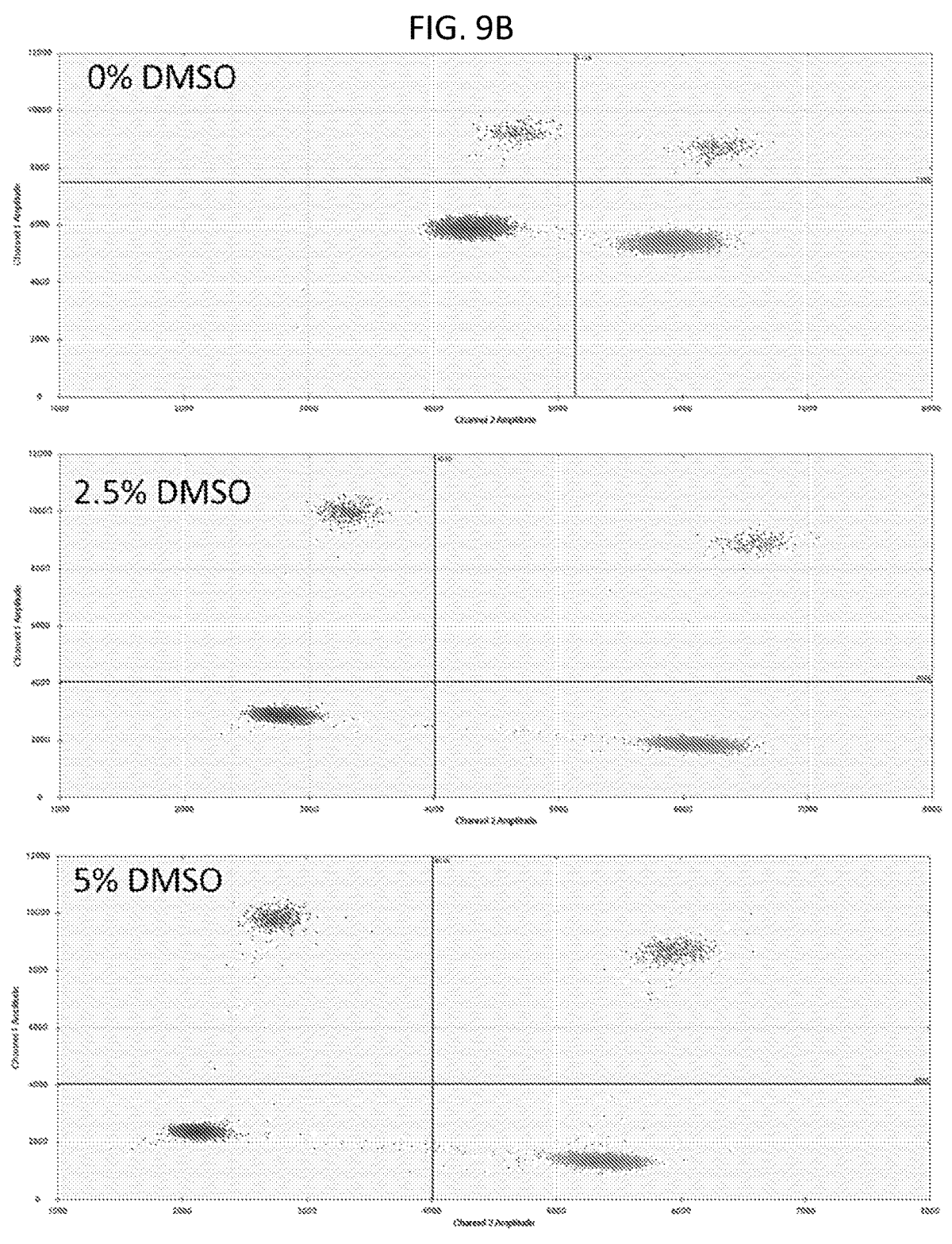

The pH of 5% Chelex® 100 in water is 10-11. Because alkaline conditions are expected to lead to rapid RNA hydrolysis, we postulated that Tris pH 8.0 in the lowTE buffer was important to achieve the high detection rate of SARS-CoV-2 virions in the presence of Chelex® 100. Thus, we measured detectable RNA amount when virions and cells were prepared in water (FIG. 1C). Heating with Chelex® 100 only detected 20% of added virions, and 15% of the RPP30 mRNA detected in the lowTE/Chelex® 100 condition. We also simulated swab stored in the MEM alpha media. Heating in MEM alpha led to an undetectable level of viral RNA and RPP30 mRNA, possibly due to the 1.8 mM $Ca^{2+}$ and 0.8 mM $Mg^{2+}$ present in the media. Inclusion of Chelex® 100 during heating resulted in detection of >55% of viral RNA (FIG. 1C). Inclusion of 2.5-5% DMSO in the final ddPCR reaction reduced negative droplets intensity (FIGS. 9A-9B), and we also simulated swab stored in the TED10 (90% lowTE+10% DMSO) buffer, which results in 2.5% DMSO in the ddPCR reaction and thus potentially simplifies reaction setup. The viral and RPP30 RNA amounts detected in the TED10 buffer in Chelex® 100 was slightly higher than those in lowTE buffer.

Figure 1D:
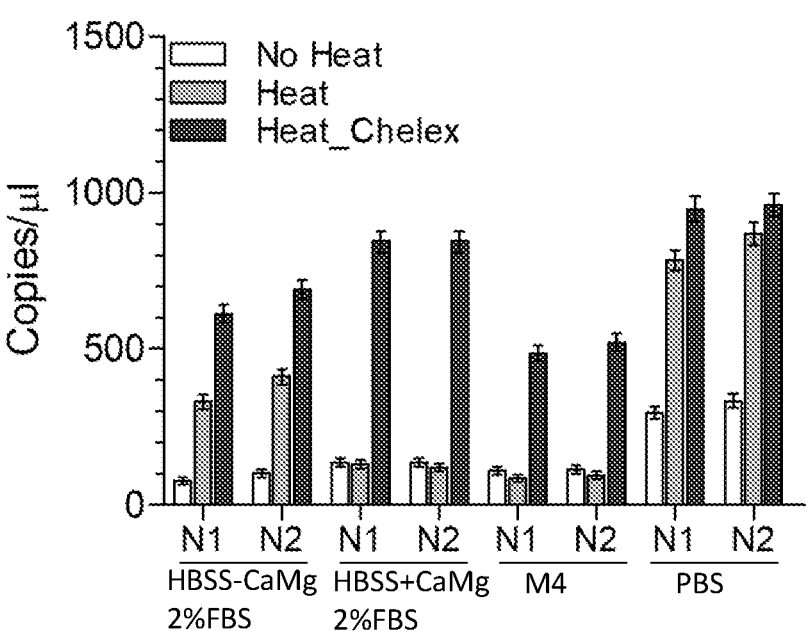
Figure 1D:
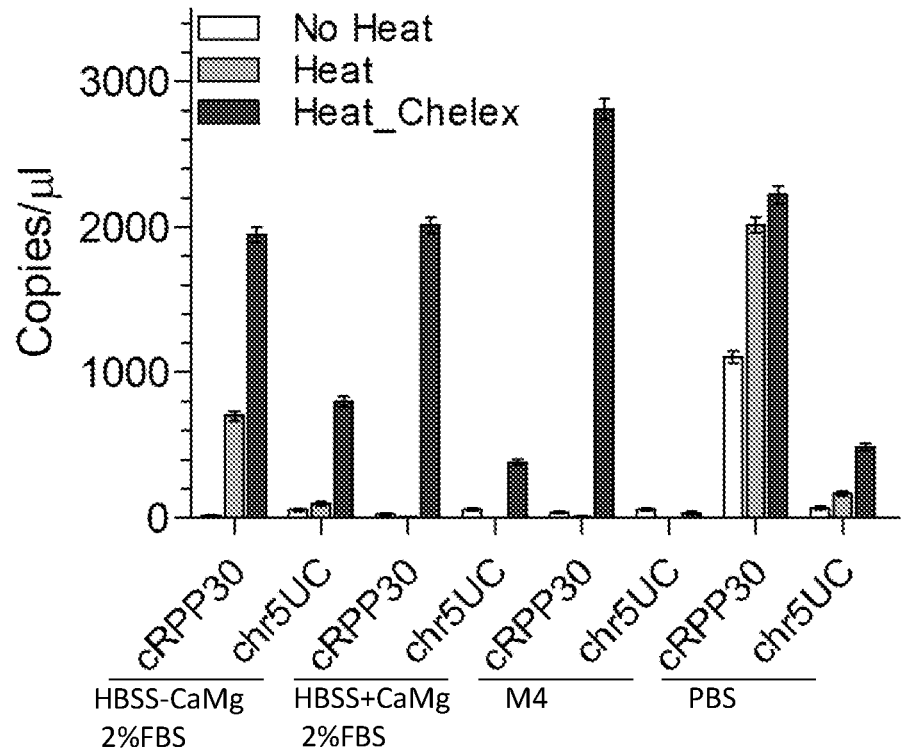

The CDC recommends VTM for specimens for viral culture and viral detection, which contains HBSS 1× with calcium and magnesium, 2% heat-inactivated FBS, Gentamicin and Amphotericin B (CDC SOP #DSR-052-05 accessed on 11/16/2020, at www.cdc.gov/coronavirus/2019-ncov/downloads/Viral-Transport-Medium.pdf). The 1×HBSS buffer contains 1.3 mM $Ca^{2+}$ and 0.9 mM $Mg^{2+}$, which may lead to viral RNA degradation during heating, similar to MEM a medium. We tested the HBSS buffer without $Ca^{2+}/Mg^{2+}$ but supplemented with 2% heat-inactivated FBS, HBSS buffer containing $Ca^{2+}/Mg^{2+}$ and 2% heat-inactivated FBS, the M4 transport medium (HBSS based medium, containing HEPES, BSA, gelatin, and antibiotics), and PBS in the RNA-extraction free assay (FIG. 1D). Heat increased viral detection for calcium/magnesium free media, but not the calcium/magnesium media. Only ~12% of viral RNA was detected in the HBSS containing $Ca^{2+}/Mg^{2+}$ and 2% heat-inactivated FBS after heating, in contrast, heating in the presence of Chelex allowed the detection of 84% of virions.

In summary, LowTE pH 8.0 and TED10 with Chelex produced the highest amounts of viral RNA detected as compared to no heat or heating conditions among the buffers tested.

Figure 2:
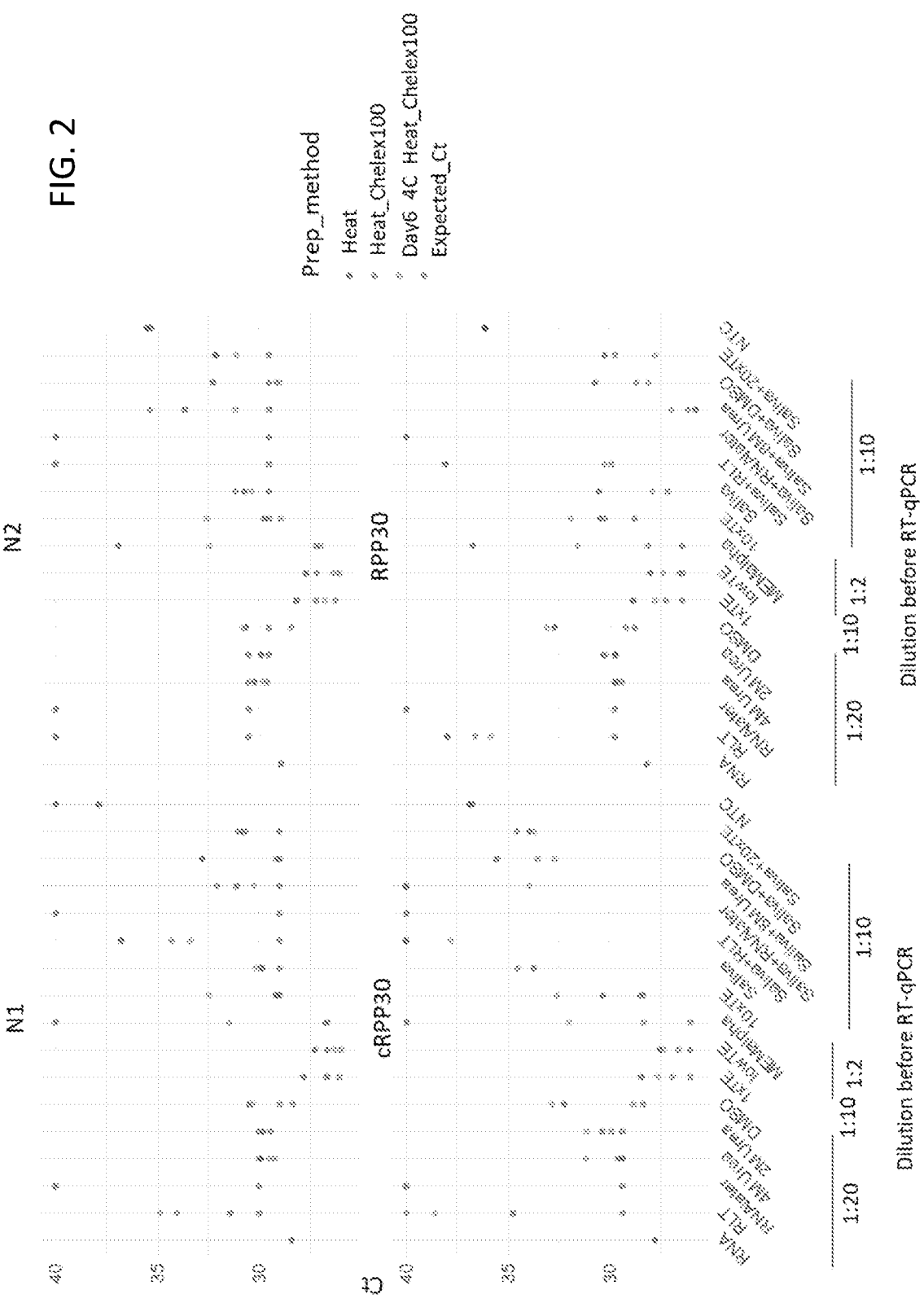
FIG. 2 shows SARS-CoV-2 prepared in different buffers used for RT-qPCR without RNA-extraction. Day6_4 C_Heat_Chelex®100 refers to samples stored at 4° C. for 6 days and then heated in 5% Chelex® 100 before RT-qPCR. Ct (Crossing threshold) values for N1 & N2 (viral targets) were set at 0.1 ΔRn, Ct values for cRPP30 (specific for RPP30 cDNA) and RPP30 (targets both genomic DNA and cDNA) were at 0.02 ΔRn. Samples were diluted in $H_2O$ as indicated at the bottom. Expected_Ct refers to Ct calculated based on Ct from extracted RNA normalized with added virion numbers after dilution using the ΔCt method. Samples with undetermined Ct values were plotted as Ct 40.

To know whether other chemicals could 1) also be used in storage of patient swabs that could be used in RNA-extraction free method, and 2) also protect RNA from degradation, we tested various buffers for RT-qPCR without conventional RNA extraction. These buffers included RNAlater (reagent used for sample storage before RNA extraction), buffer RLT (lysis buffer from the RNeasy® RNA extraction kit), urea (used for RNA extraction previously), DMSO (used as lysis buffer for DNA extraction, and known to inhibit RNases), 1×TE (10 mM Tris, 1 mM EDTA, pH 8.0), 10×TE (20 mM Tris, 10 mM EDTA, pH 7.5), and MEM alpha medium (mimic of viral transport medium). Inactivated SARS-CoV-2 and 293FT cells were mixed and added to these buffers above along with lowTE and heated with or without Chelex® 100 (FIG. 2). Inactivated SARS-CoV-2 virions were also added to saliva pre-mixed 1:1 with various buffers to test whether saliva samples can be subjected to direct RNA detection. We diluted the samples in water before RT-qPCR to avoid suspected inhibition of reverse transcription and PCR, and then compared the Ct values to calculated Ct values based on Ct of extracted RNA and number of virions present in each sample.

Of the chemicals tested, RNAlater and RLT appeared to be not compatible with the RNA-extraction-free method, as there was either no amplification or the Ct values were much higher than for all four targets (FIG. 2) after 20-fold dilution. Urea, DMSO, TE or MEM alpha showed minimum RT-qPCR inhibition after dilutions. Interestingly, Chelex® 100 appears to be critical to achieve better detection of viral RNA and cellular RNA in DMSO, 1×TE, lowTE, or MEM alpha, with the average Ct cycle difference of N1 & N2 between Chelex® and heat alone as 2.2, 1.8, 1.4, and 13, respectively. This represents improvement of sensitivity by Chelex® 100 of 4.5, 3.6, 2.7, and >1000 fold for samples prepared in DMSO, 1×TE, lowTE and MEM, respectively. Samples were also stored at 4° C. for 6 days and then subjected to heat with Chelex® 100 and RT-qPCR. The viral RNA amounts in DMSO, 1×TE, lowTE, or MEM alpha were reduced by 77%, 32%, 21%, and 97%, respectively, after 6 days at 4° C. The viral RNA appeared stable at 4° C. in Urea as there was no reduction observed. The cellular RPP30 RNA was less stable than viral RNA and showed 40% reductions in 1×TE or lowTE and over 90% in DMSO or MEM alpha (FIG. 2).

Saliva samples without exogenous chemicals or in DMSO showed to be best for RT-qPCR among the tested conditions (FIG. 2). Chelex® 100 at 5% did not improve Ct for saliva, while it decreased 3.4 Ct cycles for saliva 1:1 mixed with DMSO (FIG. 2). Both viral and RPP30 RNA molecules in saliva were stable for 6 days at 4° C. without preservatives, or in DMSO. Comparing the observed Ct values to the expected Ct values suggests that ~50% of viral RNA were detected in saliva without other chemicals added, and 1:1 dilution of saliva with DMSO allowed ~100% viral RNA to be detected.

Figure 3:
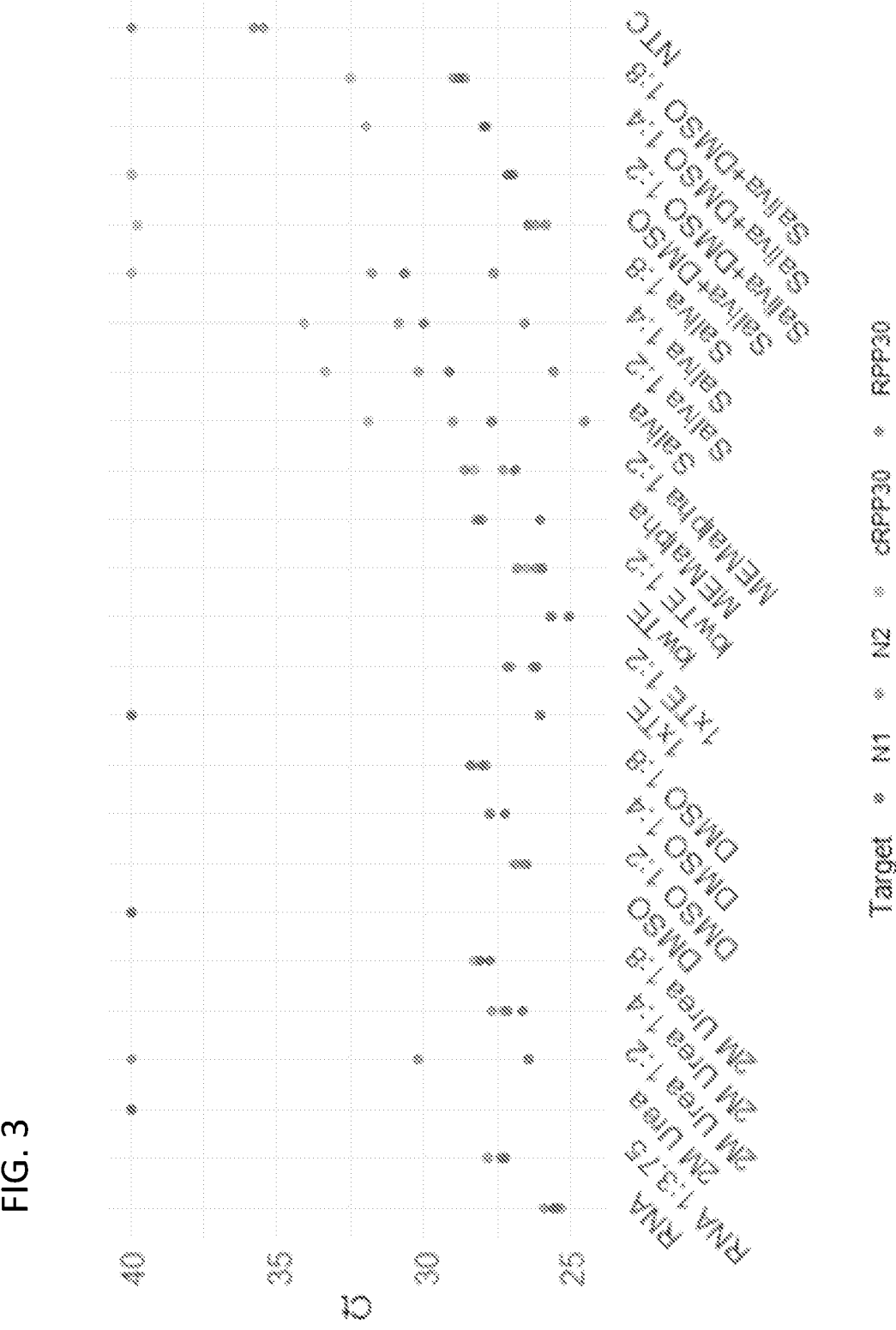
FIG. 3 illustrates buffer compatibility in RT-qPCR. Ct values of samples heated in the presence of Chelex® 100 are shown. Ct (Crossing threshold) values for N1 & N2 (viral targets) were set at 0.1 ΔRn, Ct values for cRPP30 (specific for RPP30 cDNA) and RPP30 (targets both genomic DNA and cDNA) were at 0.02 ΔRn. Samples were diluted in $H_2O$. Samples with undetermined Ct values were plotted as Ct 40.

We next determined the maximum concentrations of tested chemicals that were tolerated in a RT-qPCR reaction (FIG. 3). For comparison, we prepared a solution of RNA, in 5 µl of which contained materials extracted from 6,250 virions (Sample RNA in FIG. 3). The undiluted samples without RNA extraction also contained 6,250 virions per 5 We used the following procedure to exemplify a conventional RNA extraction RT-qPCR method. A swab was added to 3 ml of UTM, of which 200 µl were used to RNA extraction, and RNA was eluted in 50 µl H₂O. This conventional method would have used 5 µl of RNA from 1,667 virions for a RT-qPCR reaction (Sample RNA 1:3.75 in FIG. 3). The rest of the samples were heat-treated with Chelex® 100 and serial dilutions of 2-fold were used for RT-qPCR. The highest chemical concentrations that did not interfere with RT-qPCR if using 5 µl of undiluted sample in a 20 µl reaction were Urea 0.5 M, DMSO 50%, EDTA 0.5 mM (FIG. 3). 1:2 dilution of samples in MEM alpha into water may provide better sensitivity than using undiluted samples because the Ct for N2 was higher in the undiluted MEM alpha than in the 1:2 dilution, although the N1 Ct was lower in the undiluted MEM alpha (FIG. 3). The N1 and N2 Ct values for the undiluted sample in lowTE was the lowest, lower than RNA-extraction using the same amount of virions. This was probably due to RNA loss during RNA extraction.

Together these results indicate that Chelex® 100 can greatly increase RNA molecules available for RT-qPCR in a variety of buffers. Collecting swabs in lowTE may provide the highest sensitivity.

Example 3

Limit of Detection and Sample Stability

We attempted to further refine the buffer recipe for RNA-extraction free method by adjusting DMSO concentration and combining TE together with DMSO. In addition, we compared the RNA-extraction free method with conventional RNA-extraction method. To this end, 200,000, 20,000, 2000, or 200 virions were added to 200 µl lowTE, 50% DMSO, 40% DMSO, TED40 (10 mM Tris pH 7.5, 0.1 mM EDTA, 40% DMSO), MEM alpha, or saliva, making a 1,000 cp/µl to 1 cp/µl concentration series. The virion-loaded saliva samples were then mixed 1:1 with 100% DMSO, 80% DMSO, 2×TED40, or 1×TE pH7.5. Another set of 200,000 to 200 virion series were used for RNA extraction following the conventional protocol described above. The samples with the highest viral loads group were then either directly used for RT-qPCR, heated, or heated with Chelex® 100.

Figure 4:
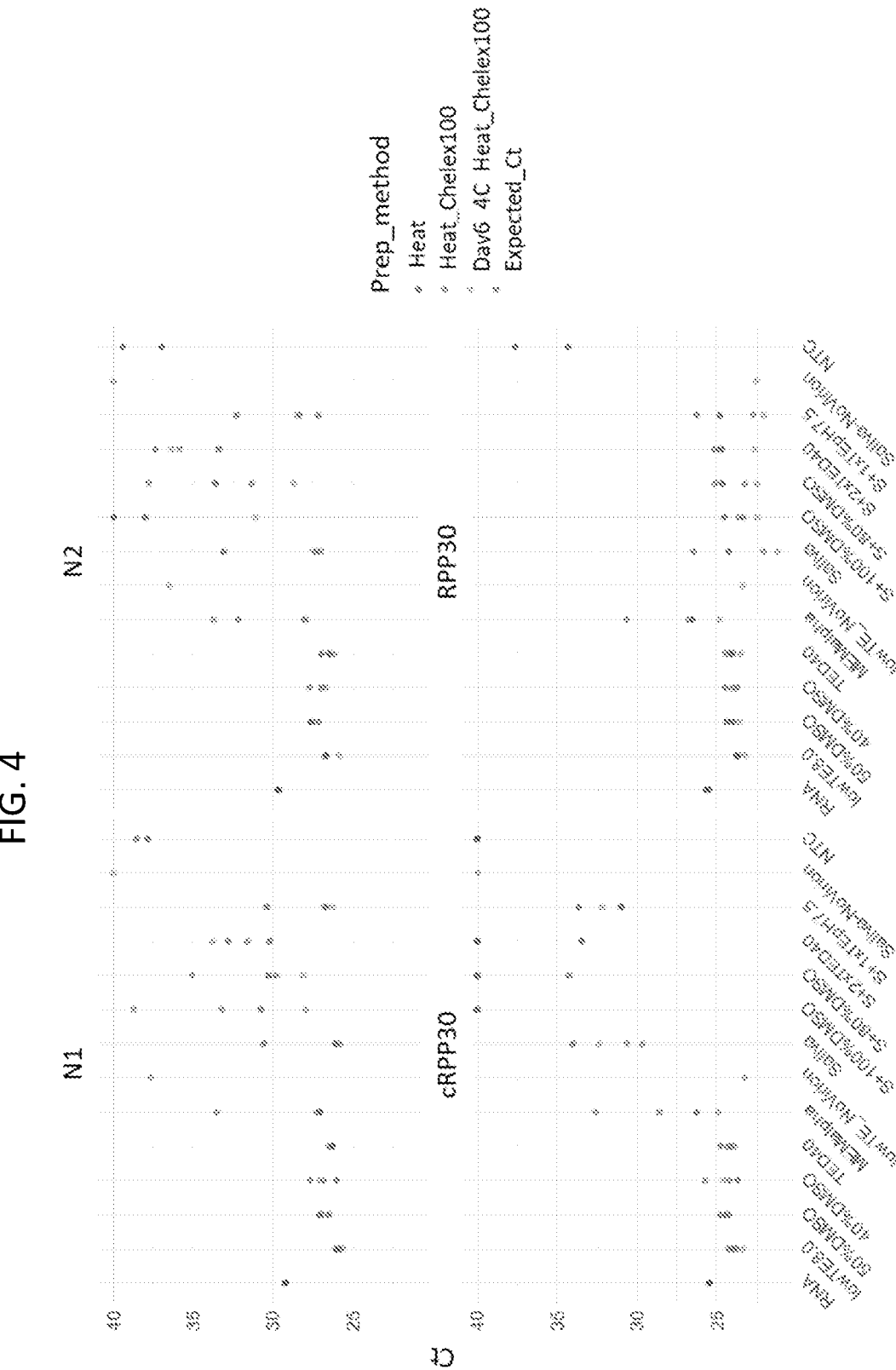
FIG. 4 shows Tris EDTA and DMSO containing buffers and RNA stability at room temperature. Day3_RT_Heat_Chelex®100 refers to samples stored at room temperature for 3 days and then heated in 5% Chelex® 100 before RT-qPCR. 5 µl of samples were used for one reaction RT-qPCR except that 2.5 µl of MEM alpha samples were used. Ct (Crossing threshold) values for N1 & N2 (viral targets) were set at 0.1 ΔRn, Ct values for cRPP30 (specific for RPP30 cDNA) and RPP30 (targets both genomic DNA and cDNA) were at 0.02 ΔRn. Samples were diluted in $H_2O$. Samples with undetermined Ct values were plotted as Ct 40.

The RT-qPCR data showed that lowTE with heat and Chelex® 100 showed the lowest Ct values for N1 and N2, and combination of TE with DMSO did not improve the Ct (FIG. 4). The viral RNA amounts in lowTE, 50% DMSO, 40% DMSO, TED40, and MEM alpha reduced 18%, 20%, 32%, 7%, and 36%, respectively, after 3 days at room temperature (25° C.). Thus, TED40 buffer may be a viable transport buffer other than lowTE, that would allow room-temperature storage of viral samples. However, the RPP30 RNA was reduced by ~50% in both lowTE and TED40 buffers after 3 days at room temperature.

Among the saliva samples, DMSO-containing buffers appeared to increase the Ct values of the N1 and N2 targets, and the saliva sample without dilution had the lowest Ct for N1 and N2 (FIG. 4). Their Ct values were ~0.5 cycles above the lowTE sample. Heating of saliva samples with or without Chelex® 100 improved Ct values by more than 2 cycles as compared to no heat samples. Chelex® 100 at 5% appeared not be very effective to enhance detection of viral RNA in saliva than heating alone. However, Chelex® 100 did not increase the Ct values for N1 and N2 markedly. Thus, we included the Chelex® 100 for RNA stability and limit of detection experiments. The Ct values for N1, N2 and cRPP30 (RPP30 cDNA) decreased after storing at room temperature for 3 days (FIG. 4), which was also observed after storing saliva samples at 4° C. for 6 days (FIG. 2). In contrast, the Ct from RPP30 targeting both genomic DNA and cDNA increased after extended storage (FIGS. 2 and 4). This is possibly because some molecules in saliva that interfere with RT-qPCR degraded during storage.

Ten-fold serial dilutions of SARS-CoV-2 virions were used to determine the lower limit of detection (LoD) of this preparation method by RT-qPCR (FIG. 5). If using conventional RNA extraction method, the LoD was 20,000 genome copies per swab. Using lowTE-Heat-Chelex®100 protocol, the LoD was 2000 copies per swab or 10 copies/μl of samples before RT-qPCR. The lowTE-Heat-Chelex®100 procedure was also able to detect 10 copies/μl virions in saliva (FIG. 5A).

Figure 5A:
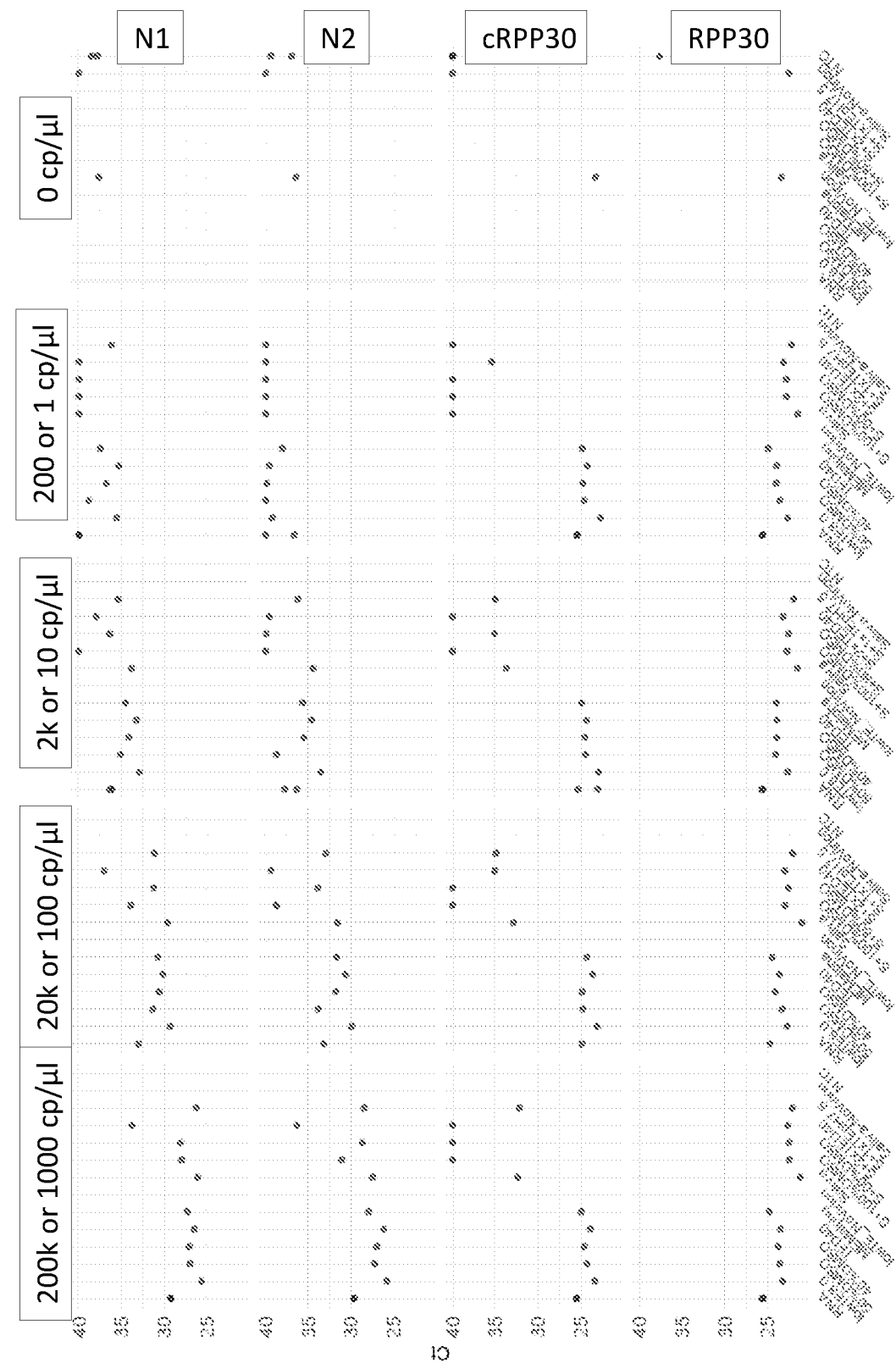
FIGS. 5A-5D show the limit of detection of SARS-CoV-2 using RT-qPCR.
Figure 5B:
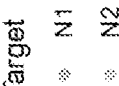
Figure 5C:
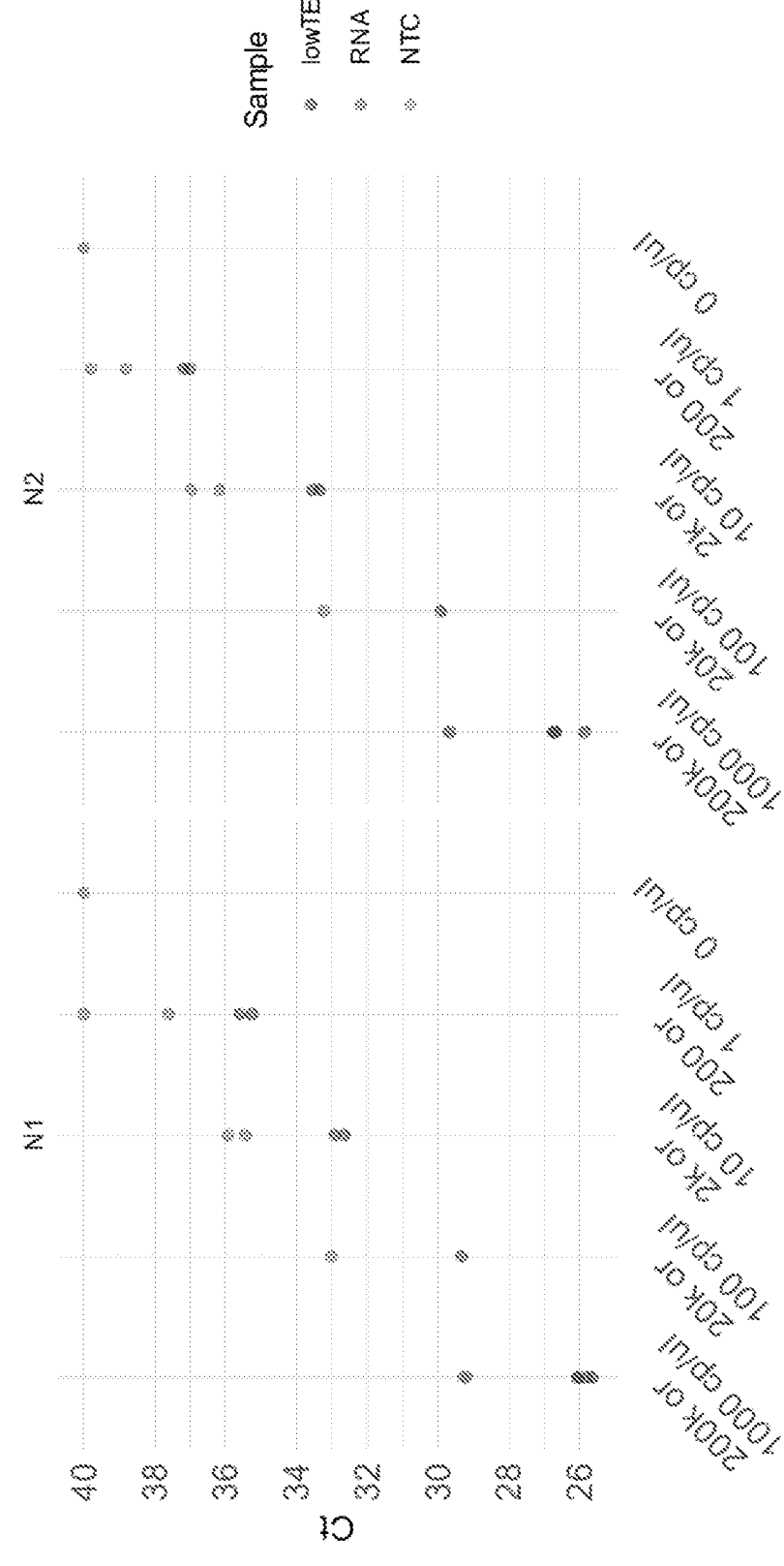
Figure 5D:
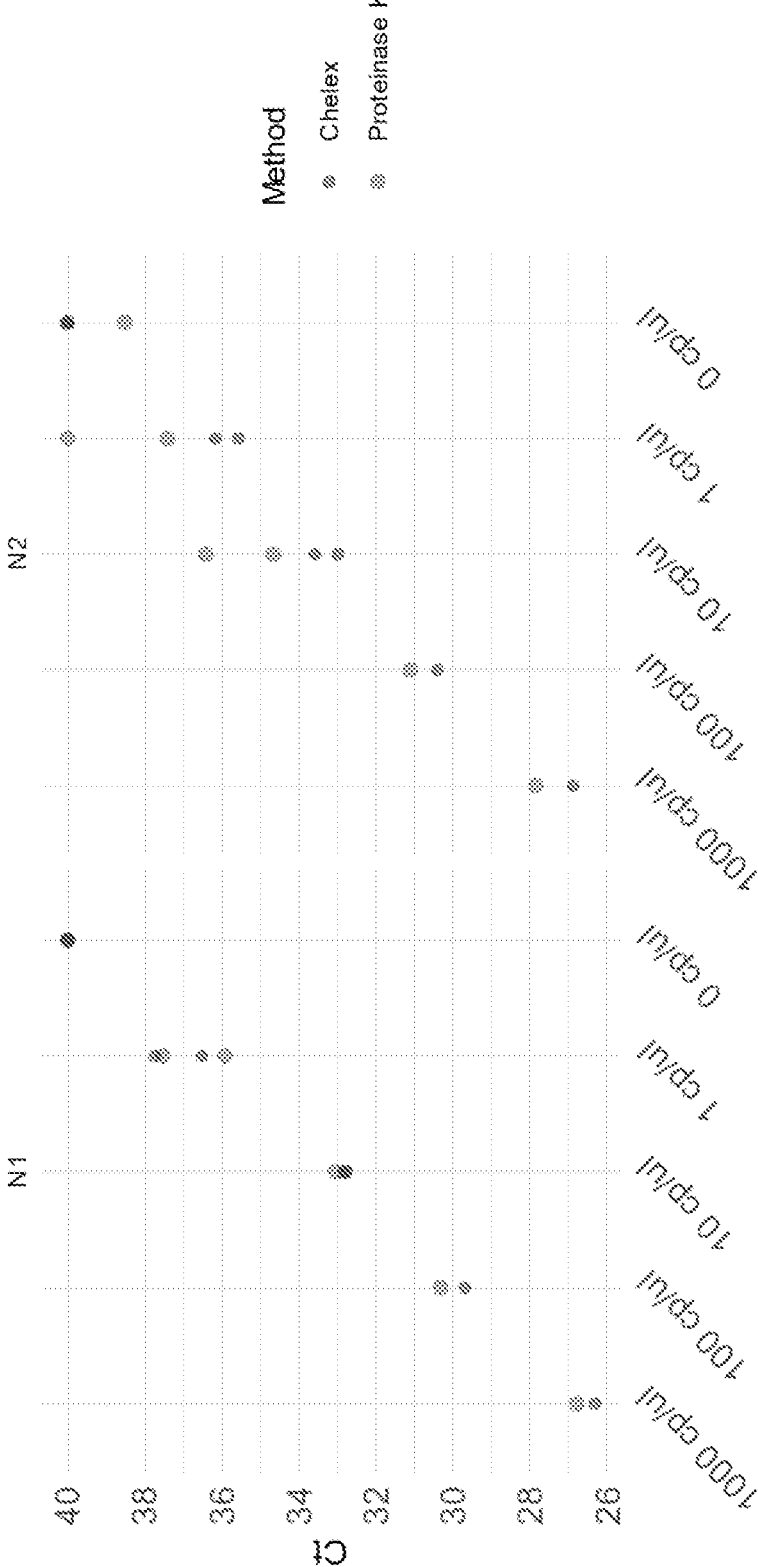

To improve the limit of detection for RT-qPCR, we optimized the reaction conditions by (i) including 2.5% DMSO in the final reaction if a sample did not contain DMSO, (ii) reducing the reaction volume to 10 (iii) using the NEB-Luna-program II for RT-qPCR, reducing denaturing time from 10 seconds to 5 seconds and annealing/extension time from 40 seconds to 20 seconds (FIG. 5B). Under this condition, the Ct for Non-template controls were either undetermined or above 38. When analyzing the 10-fold serial dilutions of SARS-CoV-2 virions using our new preparation method by RT-qPCR, the LoD was 200 copies per swab or 1000 copies/ml of samples before RT-qPCR (FIG. 5C). Using the conventional RNA extraction method, the LoD was 2,000 genome copies per swab or 667 copies/ml of samples in VTM (FIG. 2A). The LoD for saliva samples using the Chelex method was also at 1000 copies/ml for all replicates when 50 μl whole unstimulated saliva was added to 25 μl of 50% Chelex, compared to the proteinase K method, which was undetermined for a single 1000 copies/ml replicate (FIG. 5D).

Figure 6:
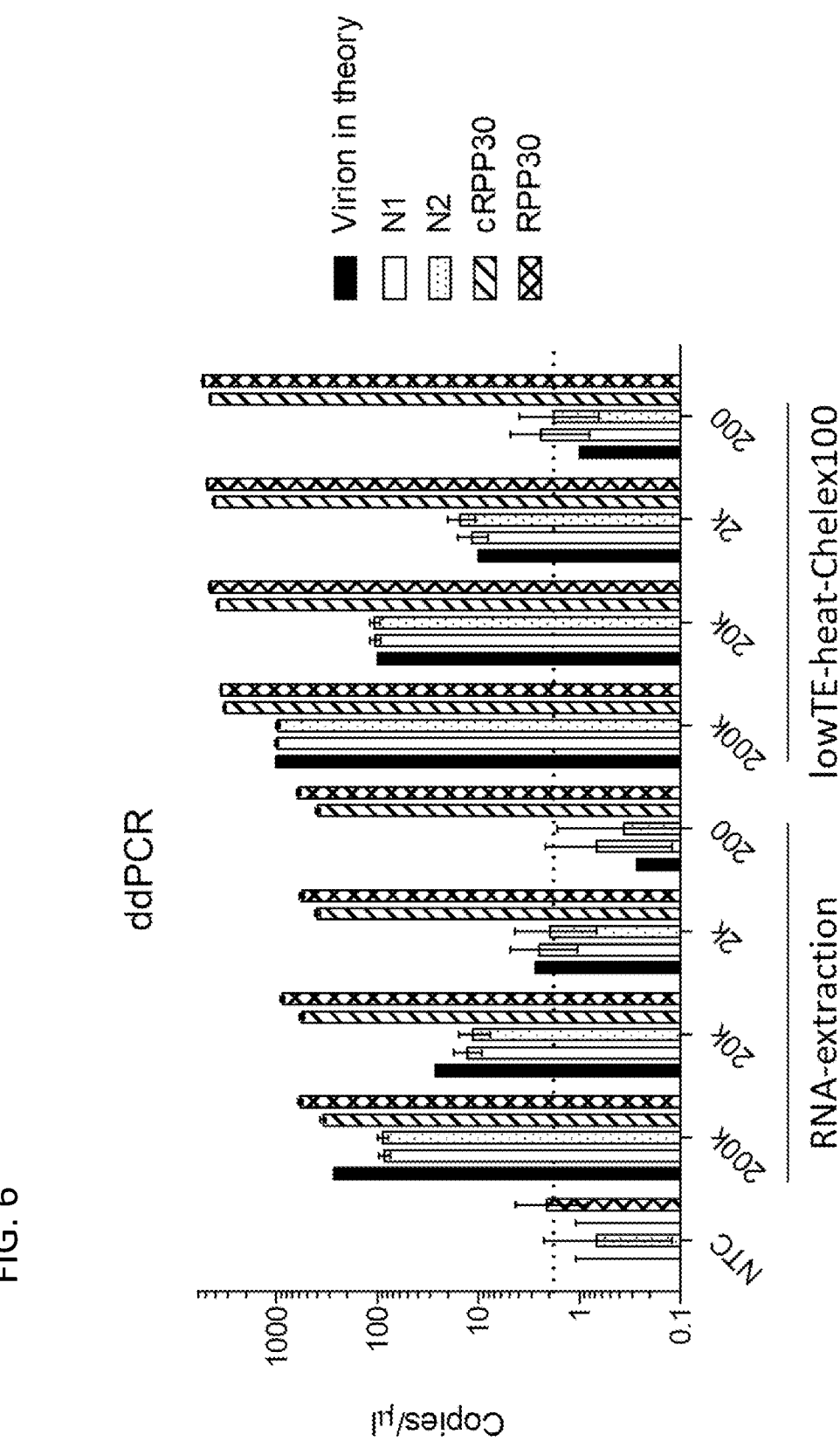
FIG. 6 shows the limit of detection of SARS-CoV-2 using RT-ddPCR. RNA-extraction refers to the procedure as in FIG. 5, simulating a swab added to 3 ml of VTM, of which 200 µl were used for RNA extraction, and RNA was eluted in 50 µl $H_2O$. 5 µl RNA was then used for RT-ddPCR in 20 µl reaction volume. LowTE-heat-Chelex®100 refers to simulating a swab procedure eluted in 200 µl lowTE, and then heated in the presence of 5% Chelex® 100. 5 µl of sample was used for RT-ddPCR in 20 µl reaction volume. The mean genome copies/µl of N1 and N2 were less than 1.2 in negative controls without virions added. Copies/µl refers to concentration in the samples used for RT-ddPCR. The error bars represent Poisson 95% confidence intervals. Dashed line indicates the threshold for the low detection limit of 1.8 copies/µl of SARS-CoV-2 virions.

We further used RT-ddPCR to determine whether we could detect a lower virion copy number. The lower limit of quantification in the 1-well RT-ddPCR assay system used is 4 copies/μl of a molecule. The means of N1 and N2 copy numbers for the control samples without virions added were less than 1.2 copies/μl (FIG. 1B and FIG. 6), thus, we applied 1.8 copies/μl, or 50% higher than the maximum N1/N2 mean of negative controls, for the mean of N1 and N2 as the threshold for being positive for the SARS-CoV-2 N1/N2 RT-ddPCR assay. RT-ddPCR decreased the LoD for conventional method with RNA extraction to 2,000 virions per swab and the lowTE-Heat-Chelex®100 method to 200 virions per swab (FIG. 6 and Table 2). The higher LoD associated with conventional method with RNA extraction was due to two reasons, (i) dilution in the VTM, and (ii) loss of RNA during RNA extraction. The RNA extraction only had 30-50% of all molecules recovered at the viral loads tested (Table 2).

TABLE 2

Limit of Detection comparing conventional RNA extraction and new preparation method

| "Swab" viral load (genome copies) | RNA-extraction | | | lowTE_Heat_Chelex ®100 | | |
|---|---|---|---|---|---|---|
| | Theoretical virus concentration* (copies/μl) | Mean of N1/N2 concentration (copies/μl) | Percentage detected | Theoretical virus concentration* (copies/μl) | Mean of N1/N2 concentration (copies/μl) | Percentage detected |
| 200k | 266.7 | 86.8 | 33% | 1000 | 976 | 98% |
| 20k | 26.7 | 12.0 | 45% | 100 | 106 | 106% |
| 2k | 2.7 | 2.2 | Detectable# | 10 | 13.4 | 134% |
| 200 | 0.3 | 0.5 | ND# | 1 | 2.1 | Detectable# |

*Virus concentration in samples used for RT-ddPCR if there is no loss during sample processing.

ND, not detectable. The means of N1 and N2 copy numbers for the control samples without virions added were less than 1.2 copies/μl, thus, 1.8 copies/μl was applied as the low limit of detection for the SARS-COV-2 N1/N2 RT-ddPCR assay.

Figure 7A:
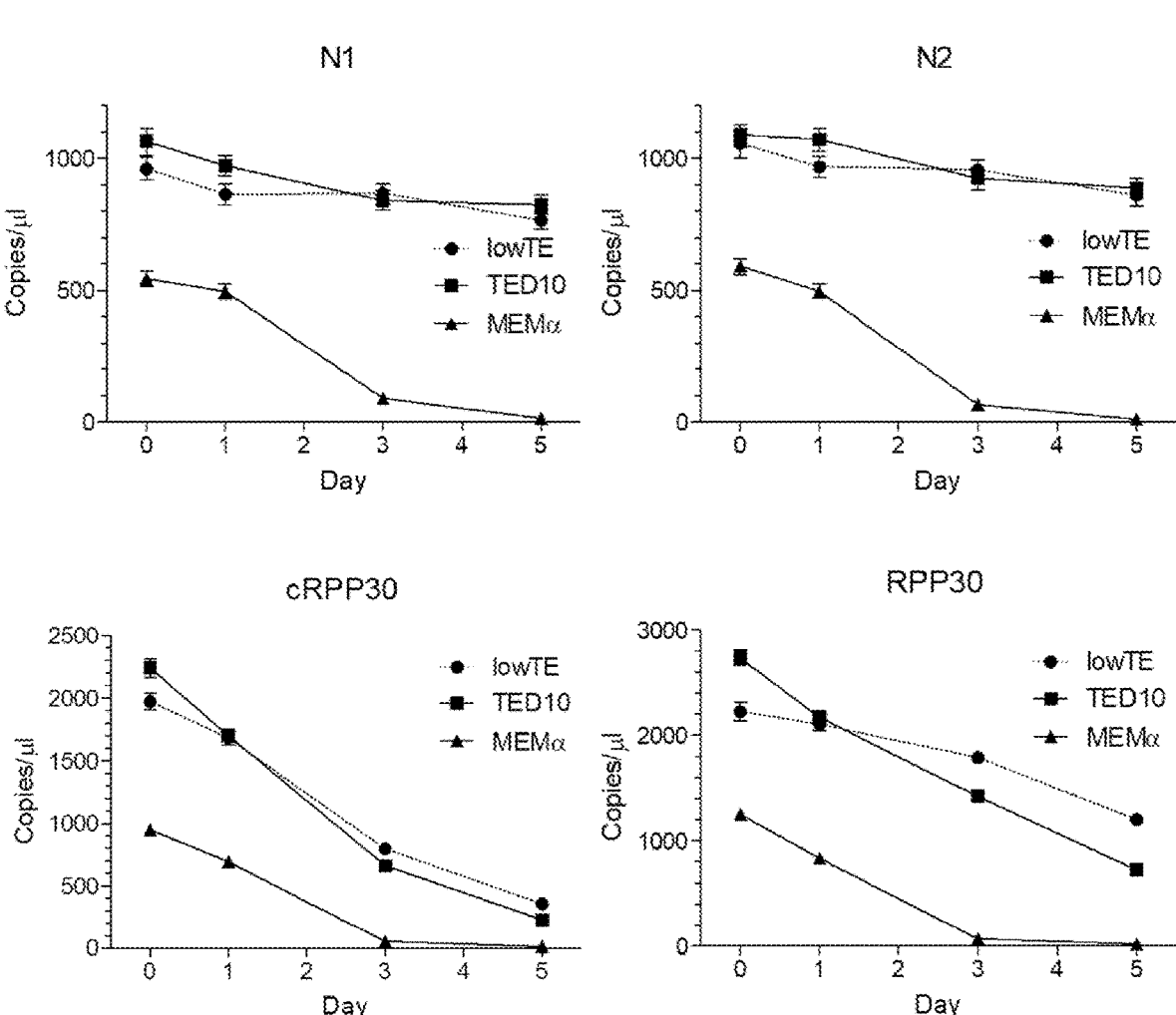
FIGS. 7A-7B show viral and cellular RNA stability in lowTE by RT-ddPCR assays.
Figure 7B:
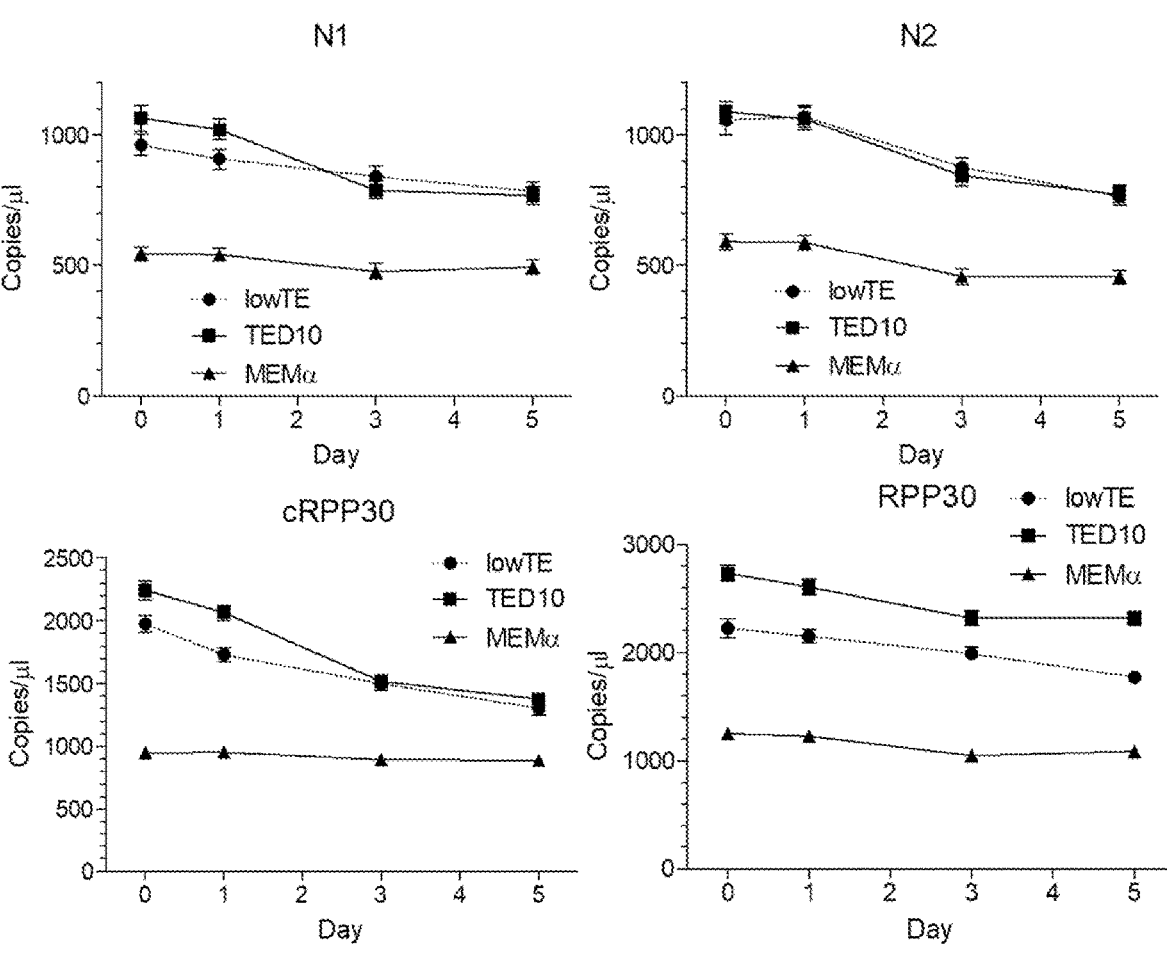

We then determined whether viral and cellular RNA were stable in a time-course experiment in more detail. In FIG. 7A, samples were stored at room temperature then heat-treated in the presence of Chelex® and assayed on the days indicated. Viral RNAs in lowTE or TED10 were relatively stable at room temperature and ~80% of N1 or N2 RNAs were detected on day 5 (FIG. 7A). Viral RNAs were less stable in MEM alpha medium as >80% were degraded after 3 days (FIG. 7A). The cellular RNA was less stable than viral RNA in the similar conditions (FIG. 7A). We then determined the RNA stability at room temperature after heat-treatment with Chelex® (FIG. 7B). Heat-treatment stabilized both viral and cellular RNA, and >80% viral RNAs and >60% cellular RNA were detected on day 5 (FIG. 7B).

Figure 8A:
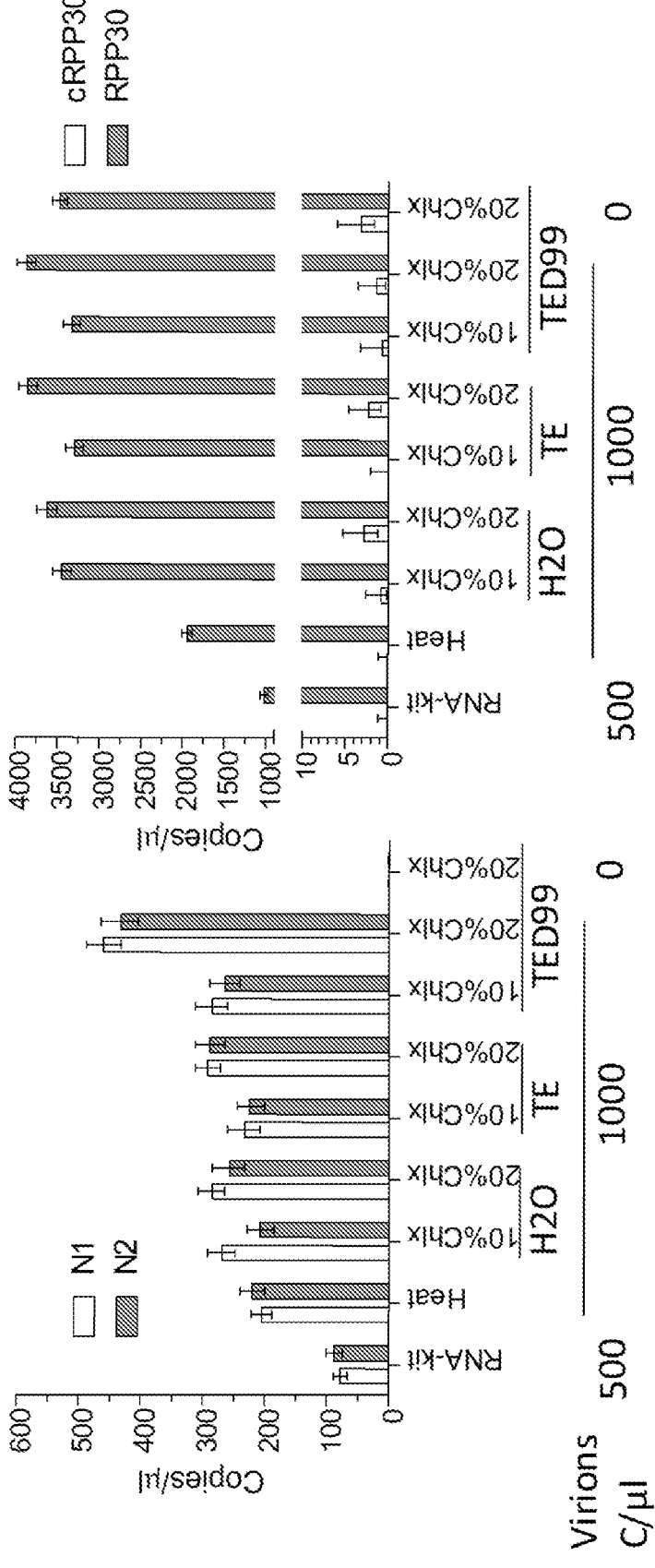
FIGS. 8A-8C show viral RNA stability in saliva by RT-ddPCR assays.
Figure 8B:
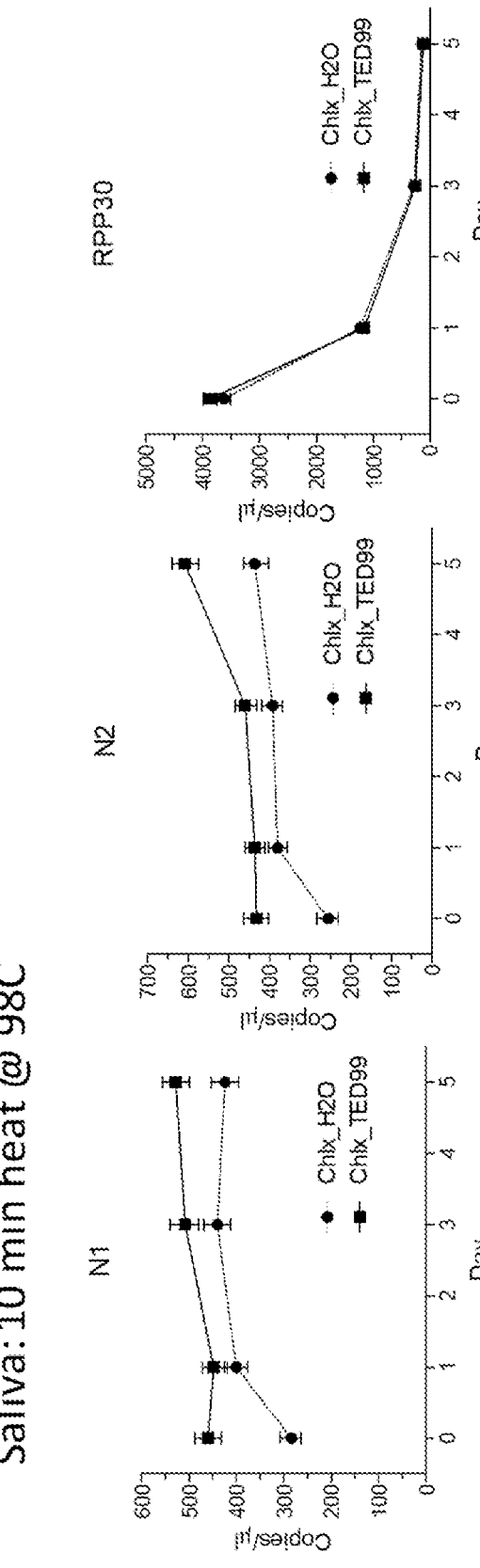
Figure 8C:
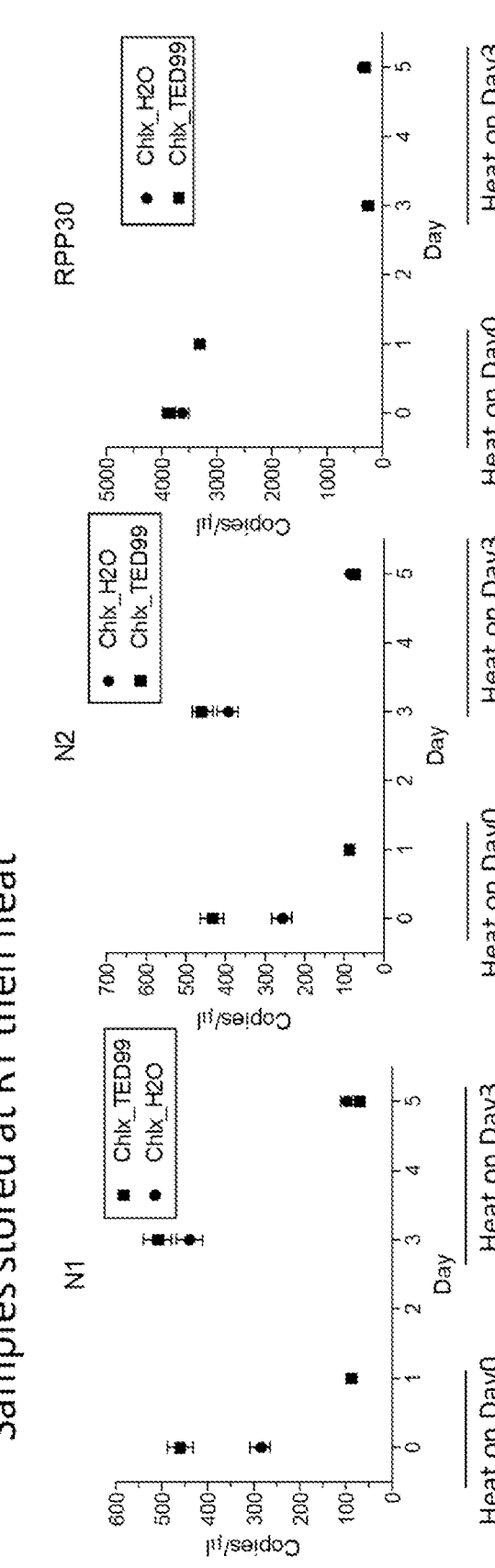

A similar stability experiment was also performed for virions prepared in saliva samples (FIGS. 8A-8C). Because the RPP30 mRNA was very low under the assay condition, the cellular RNA stability was not analyzed. The viral RNAs were stable in saliva before heat-treatment, as a higher amount of viral RNAs were detected after storage at room temperature, however, the viral RNA stability decreased markedly after heat treatment (FIGS. 8A-8C).

Example 4

Detection of SARS-CoV-2 in Primary Patient Samples

The Chelex RNA preparation method was validated using primary patient samples. NP swabs were collected in M4 (N=14, S01 to S14, FIG. 11A) or PBS (N=2, S15 & S16). These samples were tested in the NIH Clinical Center diagnostic laboratory using conventional CDC RNA extraction and RT-qPCR method (easyMAG-CL method), then frozen. Three of these samples, S01 to S03, had viral titer above 200 genome copies/µl. Twelve samples had viral titer less than 20 genome copies/µl, including eight considered indeterminate because only one of N1 or N2 targets was positive. One sample, S14, was negative.

Samples were thawed and mixed with the Chelex resin, heat-inactivated, and subjected to RT-qPCR using the NEB Luna RT-qPCR kit (Chelex-Luna method). As the easy-MAG-CL method enriched sample 4-fold before RT-qPCR, we expected that Ct values from the Chelex-Luna method would increase by 2-fold including loss that may occur during RNA extraction (50% detectable viral materials in M4 in the Chelex-Luna assay; FIG. 1D). The Ct values for N1, N2, and RPP30 from clinical laboratory RT-qPCR and NEB Luna RT-qPCR were comparable when using a common set of purified patient RNA samples with different viral titer (data not shown). The mean difference of N1 Ct between the two methods was 2.7, excluding four samples (S10, S11, S12, and S16) that did not show a Ct value in the Chelex-Luna assay.

Figure 11A:
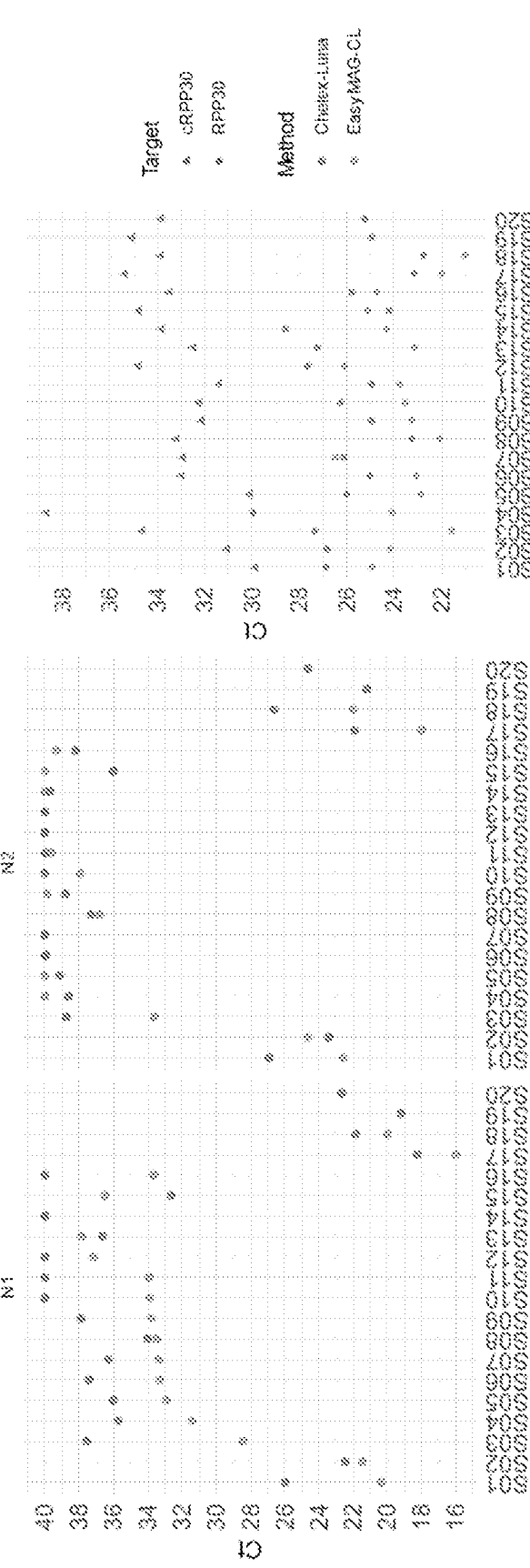
FIGS. 11A-11C shows SARS-CoV-2 detection of patient samples prepared by the Chelex method.

Of the twelve samples with less than 20 genome copies/µl, eight (or 67%) showed as positive in the N1 Chelex-Luna assay, including two samples (S13 and S15) that showed lower Ct values and another (S08) with the similar Ct value. The N2 Ct values were higher than N1 and many were higher than 38, thus were not informative for the low titer samples in the Chelex-Luna assay. Two NP swab samples stored in the CDC-suggested VTM (HBSS with Calcium & Magnesium, S17 and S18) were tested side-by-side using the easyMag-CL and Chelex-Luna methods. The N1 & N2 Ct values of both samples increased 2 and 4, respectively, reflecting likely inhibition by the VTM as observed in the synthetic samples (FIG. 11A).

Figure 11B:
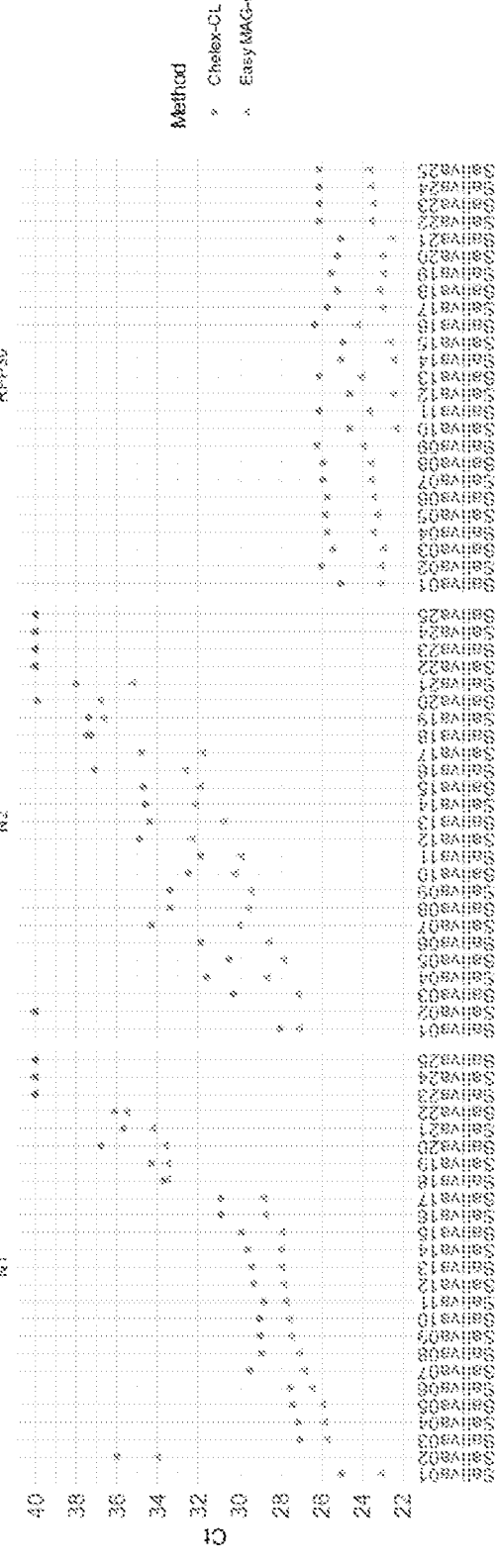

Next, the RNA extraction and Chelex methods were compared using two primary saliva samples (Saliva01 & 02) and 20 positive saliva samples diluted in negative saliva samples side-by-side (Saliva03 to 22, FIG. 11B). The mean Ct differences between the Chelex and RNA extraction methods for N1 and N2 were 1.6 and 2.6 respectively. Among the six samples with less than 10 genome copies/µl as determined by the RNA extraction method, five showed as positive and one (Saliva20) was indeterminate in the Chelex assay (FIG. 11B). Thus, the Chelex method demonstrated similar sensitivity as the RNA extraction method for both primary NP swab and saliva samples.

Figure 11C:
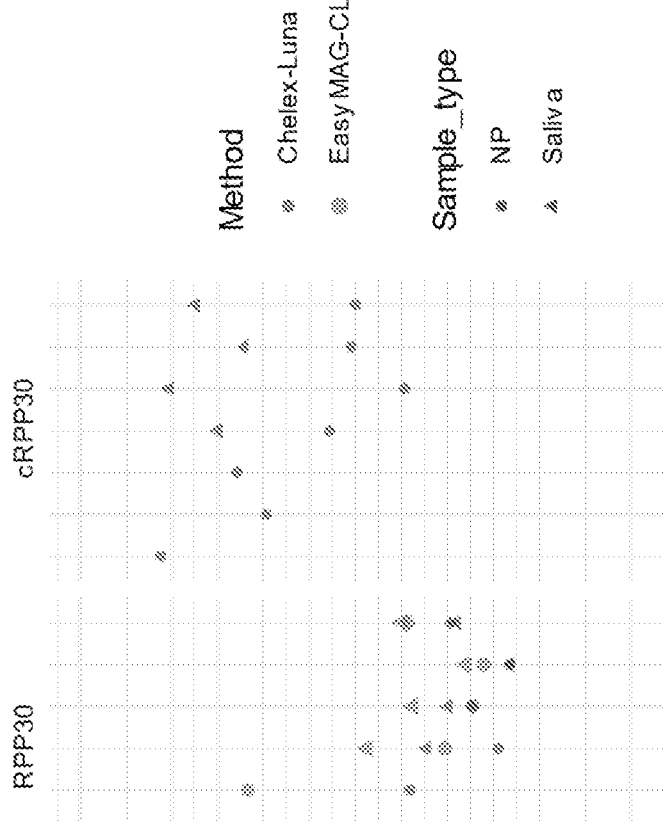
Figure 11C:
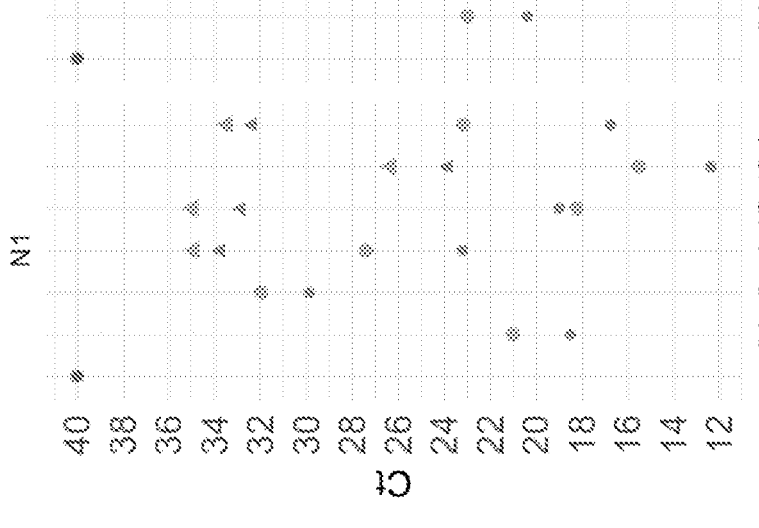

The optimized Chelex RNA isolation method was then tested prospectively by collecting symptomatic patient NP swabs (n=7) and saliva-saturated swabs (n=4) directly into 0.5 ml (NP) or 0.4 ml (saliva) Chelex containing buffer, side-by-side with swabs collected into 3 ml VTM. The Chelex samples were heated and used for NEB Luna RT-qPCR, and the samples in VTM were subjected to RNA extraction followed by RT-qPCR performed at the clinical laboratory. Because $\frac{1}{6}^{th}$ of buffer in the collection tube was used in the Chelex method and RNA extraction concentrated sample by 4-fold, the Ct values in the Chelex method are expected to be 0.6 lower than the RNA extraction method ($\frac{1}{200}$ of materials from a swab used in a 10 µl RT-qPCR reaction in the Chelex-Luna method vs $\frac{1}{150}$ of materials from a swab used in a 20 µl reaction in the EasyMAG-CL method). Sample P1 was found to be negative using both methods, and five of the six NP samples and four of the four saliva samples had lower N1 and N2 Ct values in the Chelex method as compared to the RNA extraction method (FIG. 11C). The NP sample N1 Ct differences for patients P2 to P7 between these two methods were −1.9, −2.1, −4.2, 0.8, −3.2, and −6.4, and their N2 Ct differences were −0.3, −5.5, −6.1, −0.7, −3.2, and −9.7. The saliva samples' N1 Ct differences for patients P4 to P7 between these two methods were −1.1, −2.1, −2.5, and −1.1, and their N2 Ct differences were −5.6, −3.9, −3.7, and −7.2. Thus, the Chelex method may offer better sensitivities using the procedure here. In addition, the Chelex method allowed sample processing without a Bio-safety Cabinet hood as the samples were inactivated before tube opening.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of preparing a sample for viral nucleic acid detection, comprising:

contacting the sample with a solution comprising a buffer at pH 4-10, 0-0.5 mM EDTA, and 1-50% chelating resin selected from the group consisting of styrene divinylbenzene copolymer containing paired iminodi- acetate ions, iminodiacetate resin SIR-300, and imino- diacetic acid agarose to form a mixture; and incubating the mixture at a temperature of at least 55° C. for about 1-60 minutes.

2. The method of claim 1, wherein the buffer is Tris-HCl.

3. The method of claim 2, wherein the solution comprises about 10 mM Tris-HCl.

4. The method of claim 1, wherein the solution comprises about 0.1 mM EDTA.

5. The method of claim 1, wherein the solution further comprises dimethylsulfoxide (DMSO).

6. The method of claim 5, wherein the solution comprises about 10-99% DMSO, about 10% DMSO, about 40% DMSO, or about 99% DMSO.

7. A method of preparing a sample for viral nucleic acid detection, comprising:

(a) contacting the sample with a solution comprising about 10-100% dimethylsulfoxide (DMSO), about 40% DMSO or about 50% DMSO, and 1-50% chelating resin selected from the group consisting of styrene divinylbenzene copolymer containing paired iminodiacetate ions, iminodiacetate resin SIR-300, and iminodiacetic acid agarose to form a mixture; and incubating the mixture at a temperature of at least 55° C. for 1-60 minutes; or (b) contacting the sample with a solution comprising about 0.1-0.5 M urea and 1-50% chelating resin selected from the group consisting of styrene divinylbenzene copolymer containing paired iminodiacetate ions, iminodiacetate resin SIR-300, and iminodiacetic acid agarose to form a mixture; and incubating the mixture at a temperature of at least 55° C. for about 1-60 minutes; or (c) contacting the sample with a solution comprising Hanks Balanced Salt Solution (HBSS), 2% fetal bovine serum, and 1-50% chelating resin selected from the group consisting of styrene divinylbenzene copolymer containing paired iminodiacetate ions, iminodiacetate resin SIR-300, and iminodiacetic acid agarose to form a mixture; and incubating the mixture at a temperature of at least 55° C. for about 1-60 minutes.

8. The method of claim 1, wherein the chelating resin is styrene divinylbenzene copolymer containing paired iminodiacetate ions.

9. The method of claim 1, wherein the solution comprises about 5% chelating resin.

10. The method of claim 1, wherein the mixture is incubated at about 95-100° C. or about 65° C.

11. The method of claim 1, wherein the sample comprises a biological specimen or an environmental sample.

12. The method of claim 1, wherein the mixture is stored for a period of time following incubating the mixture at a temperature of at least 55° C. for about 1-60 minutes.

13. The method of claim 12, wherein the mixture is stored at ambient temperature or about 4° C.

14. The method of claim 12, wherein the mixture is stored for about 2 hours to 7 days.

15. The method of claim 1, wherein the mixture is stored for a period of time prior to incubating at a temperature of at least about 55° C.

16. The method of claim 15, wherein the mixture is stored at ambient temperature or about 4° C.

17. The method of claim 15, wherein the mixture is stored for about 2 hours to 7 days.

18. The method of claim 1, further comprising detecting one or more nucleic acids in the mixture.

19. The method of claim 18, wherein the method comprises detecting one or more RNAs in the mixture.

20. The method of claim 18, wherein the one or more nucleic acids are viral nucleic acids.

21. The method of claim 20, wherein the viral nucleic acids are one or more coronavirus nucleic acids.

22. A kit comprising one or more containers comprising a solution comprising 10 mM Tris-HCl, 0.1 mM EDTA, and 5% styrene divinylbenzene copolymer containing paired iminodiacetate ions.

23. The kit of claim 22, wherein the solution further comprises about 10-99% dimethylsulfoxide (DMSO), 10% DMSO, about 40% DMSO, or about 99% DMSO.

24. A kit comprising one or more containers comprising a solution comprising:

10-50% dimethylsulfoxide (DMSO) and 5% styrene divinylbenzene copolymer containing paired iminodiacetate ions; or 0.1-0.5 M urea and 5% styrene divinylbenzene copolymer containing paired iminodiacetate ions; or Hanks Balanced Salt Solution (HBSS), 2% fetal bovine serum, and 5% styrene divinylbenzene copolymer containing paired iminodiacetate ions.

25. The method of claim 3, wherein the method comprises:

contacting the sample with a solution comprising 10 mM Tris-HCl pH 8.0, 0.1 mM EDTA, and 5% styrene divinylbenzene copolymer containing paired iminodiacetate ions to form a mixture; and incubating the mixture at a temperature of 98° C. for about 5 minutes.

26. The method of claim 7, wherein the chelating resin is styrene divinylbenzene copolymer containing paired iminodiacetate ions.

*     *     *     *     *